(12) United States Patent
Shimizu et al.

(10) Patent No.: US 10,307,525 B2
(45) Date of Patent: Jun. 4, 2019

(54) CONTRAST AGENT REMOVING DEVICE AND CONTRAST AGENT REMOVING METHOD

(71) Applicant: TERUMO KABUSHIKI KAISHA, Tokyo (JP)

(72) Inventors: Katsuhiko Shimizu, Fujinomiya (JP); Keiko Yamashita, Atsugi (JP); Hiroki Hosono, Hadano (JP); Yasukazu Sakamoto, Hiratsuka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 328 days.

(21) Appl. No.: 15/134,194

(22) Filed: Apr. 20, 2016

(65) Prior Publication Data

US 2016/0310658 A1    Oct. 27, 2016

(30) Foreign Application Priority Data

Apr. 22, 2015 (JP) ................................ 2015-087445

(51) Int. Cl.
| A61M 1/36 | (2006.01) |
| A61M 25/00 | (2006.01) |
| A61M 1/00 | (2006.01) |

(52) U.S. Cl.
CPC .......... *A61M 1/3615* (2014.02); *A61M 25/00* (2013.01); *A61M 1/008* (2013.01); *A61M 2202/0468* (2013.01)

(58) Field of Classification Search
CPC ................ A61M 1/008; A61M 1/3615; A61M 2202/0468; A61M 25/00
See application file for complete search history.

(56) References Cited

U.S. PATENT DOCUMENTS

| 4,834,110 | A | * | 5/1989 | Richard | ............... | A61B 5/4277 600/573 |
| 7,300,429 | B2 | | 11/2007 | Fitzgerald et al. | | |
| 2011/0213297 | A1 | * | 9/2011 | Aklog | .................... | A61B 17/22 604/28 |

* cited by examiner

*Primary Examiner* — Kai H Weng
(74) *Attorney, Agent, or Firm* — Jason H. Vick; Sheridan Ross, PC

(57) ABSTRACT

A contrast agent removing device configured to remove a contrast agent from blood vessels includes: an elongated outer tube 40; an inner tube 20 arranged in an interior of the outer tube 40; an expandable portion 30 interlocked with a distal portion of the inner tube 20 and configured to be capable of being stored within the outer tube 40 and to expand radially outward in a funnel shape opening in a distal direction by projecting from the outer tube in the distal direction; and a fixing portion 80 provided at the rim of the expandable portion 30 and configured to be capable of being fixed to a contact object.

13 Claims, 16 Drawing Sheets

CONTRAST AGENT REMOVING DEVICE AND CONTRAST AGENT REMOVING METHOD

CROSS REFERENCE TO RELATED APPLICATIONS

This application claims priority, under 35 U.S.C. 119, to Japanese Pat. App. No. 2015-087445, filed on Apr. 22, 2015, and entitled "CONTRAST AGENT REMOVING DEVICE AND CONTRAST AGENT REMOVING METHOD."

TECHNICAL FIELD

The present invention generally relates to a contrast agent removing device and a contrast agent removing method for removing a contrast agent injected into blood vessels.

BACKGROUND

In the related art, percutaneous coronary intervention (PCI) developed for restoring a blood flow is performed as a method of treatment of ischemic heart diseases such as angina pectoris and myocardial infarction. The PCI includes inserting a balloon into a stenosed site or an occluded site in a coronary artery and dilating the balloon to forcedly widen the stenosed site or the occluded site.

A contrast agent is administered to the coronary artery, and then the PCI is performed while monitoring the stenosed site or the occluded site under X-ray fluoroscopy.

When the PCI is performed for patients having a renal dysfunction, contrast-induced nephropathy may result due to side effects of the contrast agent, and in some cases, dialysis treatment may be required.

The cause is not clearly defined, but one of the conceivable causes is a vascular factors such as renal ischemia caused by decreases of renal perfusion and glomerular filtration rate as a result of the contrast agent flowing into kidney and triggering renovascular contraction.

In addition, it is also known that the contrast agent is directly cytotoxic for renal tubular cells.

Therefore, various methods for removing a contrast agent in blood vessels have been proposed.

For example, a method of sucking and draining out a contrast agent, which has been injected into the coronary artery for the PCI and flows into coronary sinus via the coronary venous, with a device inserted into the right atrium is described in U.S. Pat. No. 7,300,429.

By sucking and draining the contrast agent in the coronary sinus, the contrast agent is removed effectively before spreading out, and thus an influence of the contrast agent on a living body can be reduced.

SUMMARY

The device described in U.S. Pat. No. 7,300,429 is provided with a funnel-shaped guiding unit configured to cover an area from right atrium to the coronary sinus for guiding blood. However, since blood flows from the coronary sinus to the right atrium, the guiding unit tends to move upon reception of a force from a blood flow, and thus it is difficult to hold the guiding unit in a desirable position.

In the case where the funnel-shaped guiding unit is not provided, the contrast agent needs to be sucked only by a thin catheter. Therefore, it is difficult to suck and drain the contrast agent sufficiently.

In order to solve the above-described problem(s), it is an object of the embodiments described herein to provide a contrast agent removing device and a contrast agent removing method capable of removing a contrast agent effectively from blood vessels.

A contrast agent removing device that achieves the above-described object is a contrast agent removing device for removing a contrast agent from blood vessels, including: an elongated outer tube; an inner shaft arranged in an interior of the outer tube; an expandable portion interlocked with a distal portion of the inner shaft and configured to be capable of being stored in the interior of the outer tube and to expand radially outward into a funnel shape opening in a distal direction by projecting in the distal direction from the outer tube; and a fixing portion provided at a rim of the expandable portion and configured to be capable of being fixed to a contact object.

The contrast agent removing device configured as described above includes the fixing portion configured to be capable of being fixed to the contact object at the rim of the expandable portion, and thus can be fixed to a wall surface of the right atrium with the expandable portion expanded so as to cover an exit of the coronary sinus from the right atrium side.

Accordingly, even within the pulsed blood vessels, the expandable portion that guides blood and the contrast agent can be held at an adequate position, and thus the contrast agent flowing from the coronary sinus to the right atrium can be effectively trapped and removed.

With the fixing portion including an adsorption portion configured to apply a negative pressure to the outside in the distal direction, the position of the expandable portion that guides the contrast agent is held adequately by causing the adsorption portion to be adhered to the wall surface of the right atrium by the negative pressure, so that the contrast agent can be effectively removed from the interior of the blood vessels.

With the fixing portion including projecting portions projecting in the distal direction, the position of the expandable portion that guides the contrast agent is held adequately by causing the projecting portions to dig into the wall surface of the right atrium, so that the contrast agent can be effectively removed from the interior of the blood vessels.

With the inner shaft preferably including a draining lumen extending from the distal portion surrounded by the expandable portion to a proximal portion and a through hole formed on a proximal side with respect to the expandable portion and penetrating from the draining lumen to an outer surface, blood and the contrast agent can be guided into the draining lumen by the expandable portion to drain the contrast agent out of the body, and the blood guided into the draining lumen can be selectively returned to blood vessels through the through hole.

In addition, since blood can be selectively returned back to blood vessels through the through hole, probability of an occurrence of ischemia can be reduced.

With the inner shaft preferably including a storage portion, which corresponds to a space extending from the distal portion surrounded by the expandable portion in a proximal direction, a through hole formed on the proximal side with respect to the expandable portion and penetrating from the expandable portion to the outer surface, and an adsorbent arranged within the storage portion and configured to be capable of adsorbing the contrast agent, blood and the contrast agent are guided to the storage portion by the expandable portion, the contrast agent is adsorbed by the adsorbent, and blood passed through the adsorbent is returned from the through hole into the blood vessels.

With the expandable portion allowing liquid to flow from a distal surface side toward a proximal surface side in an expanded state and including the adsorbent capable of adsorbing the contrast agent arranged therein, the contrast agent out of a mixture of blood and the contrast agent flowing in the expandable portion can be adsorbed by the adsorbent, while the blood that has passed through the adsorbent can be returned back to blood vessels.

A contrast agent removing method for achieving the aforesaid object is a contrast agent removing method for removing a contrast agent from an interior of blood vessels including (i) an inserting step for inserting a contrast agent removing device provided with an expandable portion capable of expanding radially outward at a distal portion and a fixing portion provided on a rim of the expandable portion and configured to be fixed to a contact object into a blood vessel and guiding the device to a right atrium, (ii) a fixing step for expanding the expandable portion to cover an exit portion of a coronary sinus from the right atrium side and fixing the fixing portion to a wall surface of the right atrium, and (iii) a removing step for removing the contrast agent guided by the expandable portion.

According to the contrast agent removing method, the expandable portion that covers the exit portion of the coronary sinus from the right atrium side can be fixed to the wall surface of the right atrium by the fixing portion. Therefore, the expandable portion that guides blood and the contrast agent can be held at an adequate position, and thus the contrast agent flowing from the coronary sinus to the right atrium can be effectively trapped and removed.

With the configuration in which the fixing portion is fixed by sucking the wall surface of right atrium with an adsorption portion, which is provided on the fixing portion and configured to apply a negative pressure to the outside in the fixing step, the position of the expandable portion that guides the contrast agent can be held adequately without applying a load to blood vessels and the contrast agent can be removed effectively from the blood vessels.

With the configuration in which the fixing portion is fixed by causing projecting portions provided on the fixing portion so as to project in a distal direction to dig into the wall surface of the right atrium in the fixing step, the position of the expandable portion that guides the contrast agent can be held adequately and the contrast agent can be effectively removed from the interior of the blood vessels.

By further providing an introducing step for introducing blood guided by the expandable portion into the contrast agent removing device for removing the contrast agent before the removing step so that a contrast agent is drained out from blood vessels in the removing step if the contrast agent is contained in the introduced blood, the contrast agent can be effectively removed from the introduced blood.

In addition, since the contrast agent is drained out of blood vessels, the amount of the contrast agent to be drained is not limited. Therefore, even a large amount of the contrast agent can be effectively removed.

By further providing the introducing step for introducing blood guided by the expandable portion into the contrast agent removing device for removing the contrast agent before the removing step so that the contrast agent is adsorbed by an adsorbent which is arranged in the contrast agent removing device and is capable of adsorbing the contrast agent and the remained blood is returned back to blood vessels in the removing step, the contrast agent can be effectively removed only by causing the introduced blood to pass through the adsorbent.

DETAILED DESCRIPTION

Embodiments will be described herein below, with reference to the attached drawings.

Note that dimensional ratios of the drawings may be exaggerated and thus may be different from actual ratios for the sake of convenience of description.

A contrast agent removing device 10 is a device configured to collect a contrast agent injected into coronary artery when performing percutaneous coronary intervention (PCI) from the coronary sinus and drain the same to the outside of the body.

Note that a side of the device which is inserted into vein is referred to as "distal side" and a hand side to be operated is referred to as "proximal side".

Figure 1:
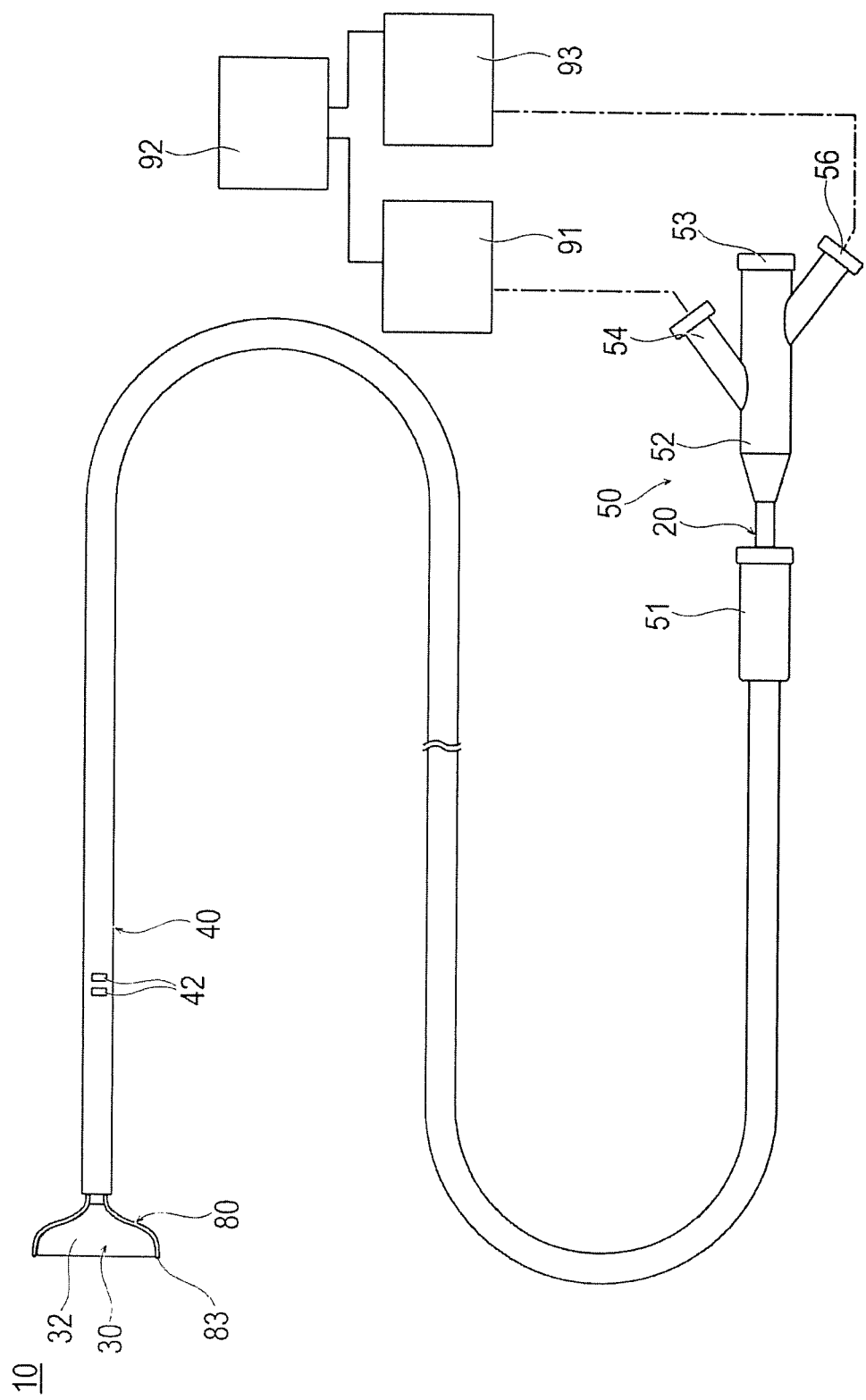
FIG. 1 is a plan view of a contrast agent removing device.
Figure 2:
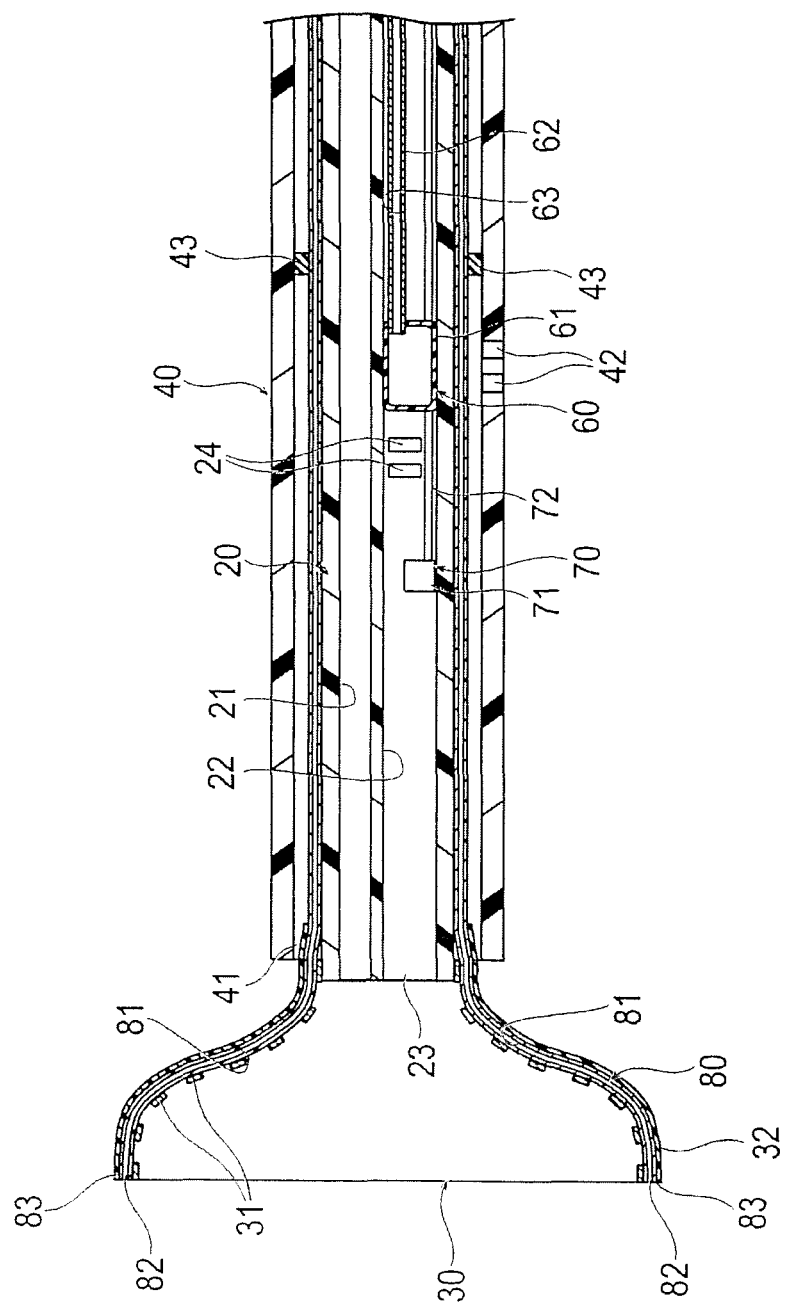
FIG. 2 is a vertical cross-sectional view illustrating a state in which an expandable portion of the contrast agent removing device is expanded.
Figure 4:
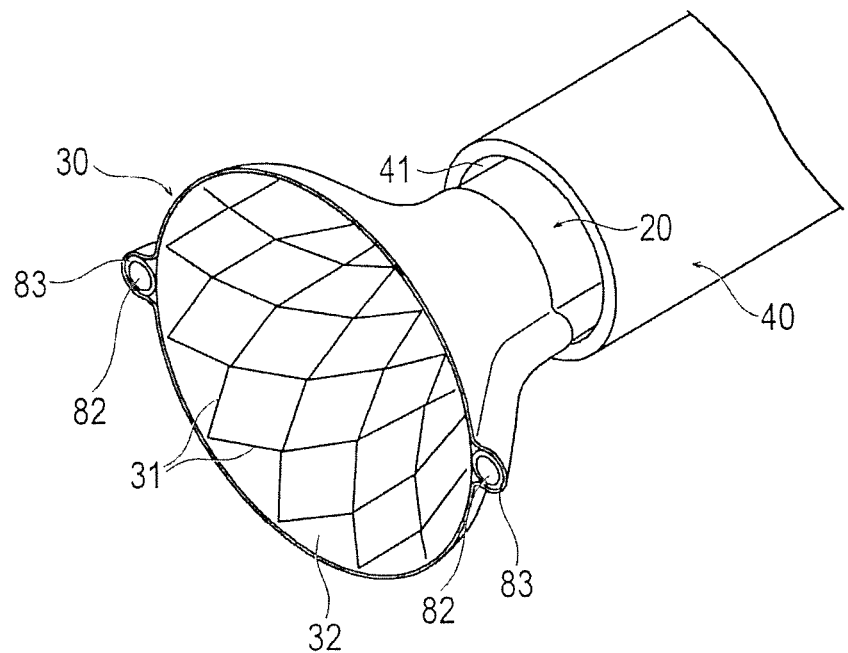
FIG. 4 is a perspective view illustrating a distal portion of the contrast agent removing device.

The contrast agent removing device 10 includes an inner tube 20 (inner shaft), an outer tube 40 configured to allow storage of the inner tube 20 in an interior thereof, an expandable portion 30 configured to be expandable and contractable at a distal portion of the inner tube 20, a valve 60 provided in an interior of the inner tube 20 and configured to be openable and closable, a detecting portion 70 configured to detect the contrast agent, a fixing portion 80 configured to fix the expandable portion 30 to a biological tissue, and an operating unit 50 for operating the expandable portion 30 as illustrated in FIGS. 1, 2, and 4.

The inner tube 20 is an elongated tubular member and includes a guide wire lumen 21 which allows insertion of a guide wire in the interior thereof, and a draining lumen 22 configured to drain the contrast agent out of blood vessels.

The inner tube 20 includes the draining lumen 22 opening at an inner tube distal side opening 23 formed on the distal side, and inner tube through holes 24 (through holes) penetrating from the draining lumen 22 to an outer surface on the proximal side with respect to the inner tube distal side opening 23.

The expandable portion 30 is interlocked with the distal portion of the inner tube 20.

A proximal portion of the inner tube 20 is interlocked with a second operating unit 52 which constitutes part of the operating unit 50.

The outer tube 40 is an elongated tubular member configured to store the inner tube 20, and to be movable in an axial direction relatively with respect to the inner tube 20.

The outer tube 40 opens at an outer tube distal side opening 41 formed on the distal side, and includes outer tube through holes 42 penetrating from the inner surface to the outer surface formed on the proximal side with respect to the outer tube distal side opening 41.

An annular seal member 43 configured to come into contact with an outer surface of the inner tube 20 to maintain liquid-tight properties is arranged in the interior of the outer tube 40 on the proximal side with respect to the outer tube through holes 42.

The proximal portion of the outer tube 40 is interlocked with a first operating unit 51 which constitutes part of the operating unit 50.

The expandable portion 30 is interlocked with an outer peripheral surface of the distal portion of the inner tube 20, and includes wire members 31 formed of elastically deformable wires and forming a net shape and a film portion 32 which covers the wire members 31 so as to close void portions between the wire members 31.

The expandable portion 30 is formed into a funnel shape which opens in the distal direction so that an outer peripheral edge projects in the distal direction from the distal portion of the inner tube 20.

Figure 3:
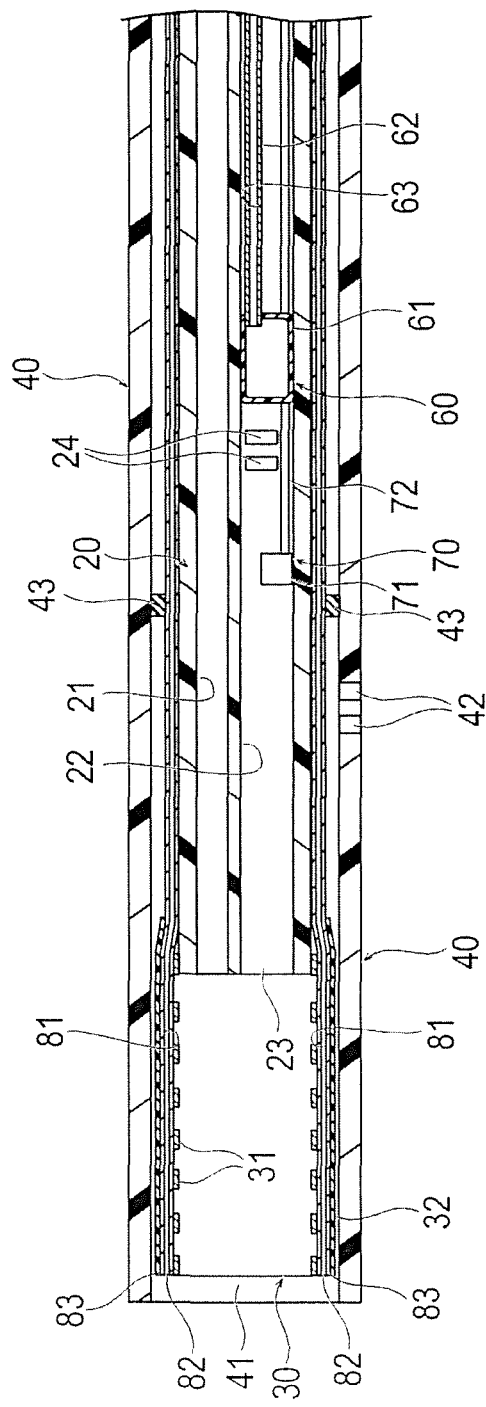
FIG. 3 is a vertical cross-sectional view illustrating a state in which the expandable portion of the contrast agent removing device is contracted.

The expandable portion 30 is stored in the outer tube 40 while being elastically deformed and contracted as illustrated in FIG. 3 by operating the operating unit 50 to move the inner tube 20 in a proximal direction relatively with respect to the outer tube 40.

The expandable portion 30 is configured to project in the distal direction from the outer tube 40 and to be elastically expandable so as to expand radially outward from the inner tube distal side opening 23 of the inner tube 20 as illustrated in FIGS. 1, 2, and 4 by operating the operating unit 50 and moving the inner tube 20 in the distal direction relatively with respect to the outer tube 40.

The detecting portion 70 includes a sensor 71 arranged in the draining lumen 22 and a signal cable 72 extending in the draining lumen 22 from the operating unit 50 to the sensor 71.

The sensor 71 is arranged on the distal side with respect to the inner tube through holes 24.

The configuration of the sensor 71 is not limited as long as the sensor 71 can detect a contrast agent, and for example, an ultrasonic sensor, an infrared ray sensor, an optical sensor, a temperature sensor, and a viscosity sensor are applicable.

The contrast agent used in this embodiment is identified by X-rays, is to be used for intravascular administer, and is a compound containing ionic or non-ionic iodine atom(s) having a molecular mass of at most approximately 8000.

More specifically, examples of the contrast agent include monomers such as iopromide, iopamidol, iomeprol, amidotrizoic acid, iohexol, iothalamic acid, iodamide, metrizoic acid, metorizoic amide, and ioxilan, and dimers such as ioxaglic acid, adipiodone, iotroxic acid, iodoxamic acid, and iotrolan. However, the contrast agent is not limited thereto.

The valve 60 includes a balloon 61 arranged in the draining lumen 22, and a dilation tube 62, which corresponds to a tubular member extending from the operating unit 50 in the draining lumen 22.

The balloon 61 is arranged on the proximal side with respect to the inner tube through holes 24 and the sensor 71.

The dilation tube 62 is provided with a dilation lumen 63 which communicates with the balloon 61 in the interior thereof, and is configured to supply a dilation fluid to the balloon 61 and to drain the dilation fluid from the balloon 61.

The balloon 61 is dilated by the dilation fluid flowing in the interior thereof to occlude the draining lumen 22, and is deflated by the dilation fluid being drained to allow the fluid to flow in the draining lumen 22.

The fixing portion 80 includes two tubular members extending in the axial direction along outer surfaces of the inner tube 20 and the expandable portion 30, and includes a suction lumen 81 in the interior of each of the tubular members.

Note that the number of the tubular members is not limited.

The fixing portion 80 includes adsorption portion(s) 83 each including an adsorption opening 82, which corresponds to an opening of the suction lumen 81 on the distal side.

The adsorption portion(s) 83 is located on a rim of the expandable portion 30, that is, at an edge of the funnel-shaped opening of the expandable portion 30.

The adsorption opening 82 opens in the distal direction, and applies a negative pressure to the outside.

The material of the inner tube 20, the outer tube 40, and the dilation tube 62 and the fixing portion 80 is preferably one of hard materials having flexibility, and polyolefin such as polyethylene and polypropylene, polyester such as polyamide and polyethylene terephthalate, fluorinated polymer such as ETFE, PEEK (polyether ether ketone), and polyimide may be used.

In order to increase rigidity, a metallic blade or a coil may be added to the above-described materials.

The material of the wire members 31 is preferably one of elastically deformable materials, and shape-memory alloy which is provided with a shape-memory effect and superelasticity by heat treatment, stainless steel, metals such as Ta, Ti, Pt, Au, and W, polyolefin such as polyethylene and polypropylene, polyester such as polyamide and polyethylene terephthalate, fluorinated polymer such as ETFE, PEEK (polyether ether ketone), and polyimide can be used.

Among others, the shape-memory alloy can be specifically.

As the shape-memory alloy, Ni—Ti based, Cu—Al—Ni based, Cu—Zn—Al based alloys can be used.

The material of the film portion 32 and the balloon 61 is not specifically limited, and natural rubber, silicone rubber, nitrile rubber, and fluorine containing rubber can be used.

The length of the contrast agent removing device 10 (the length from the distal-most portion of the inner tube 20 to the operating unit 50) is not limited, but can be in a range, for example, from 1000 mm to 2000 mm.

The outer diameter of the outer tube 40 is not specifically limited, and can be in a range from 3.0 mm to 5.0 mm.

The outer diameter of the inner tube 20 is not specifically limited, and can be in a range, for example, from 2.0 mm to 4.0 mm.

The maximum outer diameter of the expandable portion 30 in a state in which the expandable portion 30 is expanded is not specifically limited as long as it is larger than the outer diameter of an exit of the coronary sinus of a patient, and can be in a range, for example, from 20 mm to 50 mm.

The inner tube 20, the expandable portion 30, the outer tube 40, and the fixing portion 80 may be formed of a material including an X-ray imaging material.

Accordingly, the position can be figured out accurately under radiography, and the procedure is further simplified.

Examples of the preferable X-ray imaging material include, for example, gold, platinum, platinum-iridium alloy, silver, stainless, molybdenum, tungsten, tantalum, palladium, and alloy of these materials.

A marker formed of the X-ray imaging material may be arranged at any position on the inner tube 20 and on the outer tube 40.

The marker can be mounted by winding a wire formed of the X-ray imaging material around an outer surface, or by forming a pipe with the X-ray imaging material and crimping or adhering the same on the outer surface.

The operating unit 50 is provided with the first operating unit 51 interlocked with a proximal end portion of the outer tube 40 and the second operating unit 52 interlocked with a proximal end portion of the inner tube 20.

The inner tube 20 penetrates through the first operating unit 51 so as to be movable in the axial direction.

The second operating unit 52 includes a guide wire port 53 that communicates with the guide wire lumen 21 of the inner tube 20, a dilation port 54 that communicates with the dilation lumen 63, a drain port 55 that communicates with the draining lumen 22, and a suction port 56 that communicates with the suction lumen 81.

A connection cable 57 electrically connected to the signal cable 72 is drawn out from the second operating unit 52.

The connection cable 57 can be connected to a detecting apparatus 90 configured to detect the concentration of the contrast agent upon reception of a signal from the sensor 71.

The guide wire port 53 allows insertion of a guide wire.

The dilation port 54 can be connected to an automatic injection apparatus 91 configured to inject and drain the dilation fluid for dilating the balloon 61.

The automatic injection apparatus 91 is controlled by a control unit 92 and thus is capable of automatically controlling dilation and deflation of the balloon 61.

The control unit 92 is composed of, for example, a computer, which can include at least a processor and a memory.

The drain port 55 is configured to drain the contrast agent from blood vessels via the draining lumen 22.

The suction port 56 allows connection of a suction apparatus 93 to generate a negative pressure at the adsorption portions 83 for causing the expandable portion 30 to be tightly adhered to the biological tissue.

The suction apparatus 93 is, for example, a pump, and is controlled by the control unit 92.

Therefore, the negative pressure to be generated by the adsorption portions 83 can be automatically controlled by the control unit 92.

The material of the first operating unit 51 and the second operating unit 52 is not specifically limited, and for example, hard resins such as polycarbonate, polyethylene, and polypropylene can be used.

Figure 11:
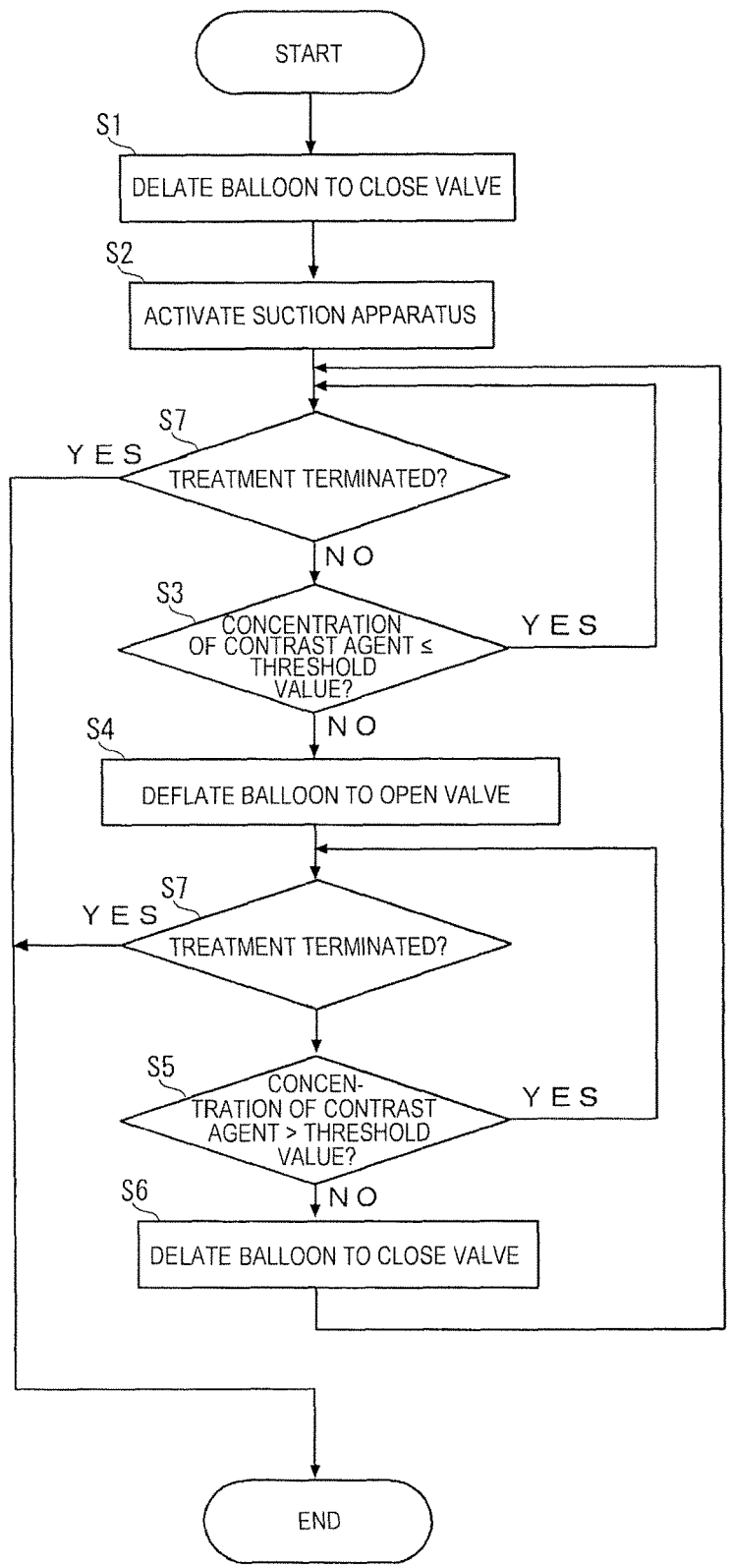
FIG. 11 is a flowchart illustrating a flow of control performed by a control unit.

Next, a method of usage of the contrast agent removing device 10 according to the first embodiment will be described with reference to a flowchart of the control unit illustrated in FIG. 11.

Here, a case of removing the contrast agent, which has been injected into coronary artery for the PCI from right atrium, will be described as an example.

Firstly, the contrast agent removing device 10 to be used is primed, and the interior is substituted by physiological salt solution. In this initial state, the expandable portion 30 is contracted and stored in the outer tube 40 as illustrated in FIG. 3. Subsequently, the automatic injection apparatus 91 is connected to the dilation port 54, the suction apparatus 93 is connected to the suction port 56, and the connection cable 57 is connected to the detecting apparatus 90 (see FIG. 1). Next, the automatic injection apparatus 91 is activated to supply the dilation fluid from the dilation port 54 and dilate the balloon 61 to bring the draining lumen 22 into a closed state (Step S1).

Next, an introducer sheath (not illustrated) is inserted into femoral vein or cervical vein. Next, a guide wire W is inserted into vein via the introducer sheath. Note that the position where the introducer sheath is to be installed is not limited as long as the contrast agent removing device 10 is allowed to access from right atrium R to coronary sinus C.

Figure 5:
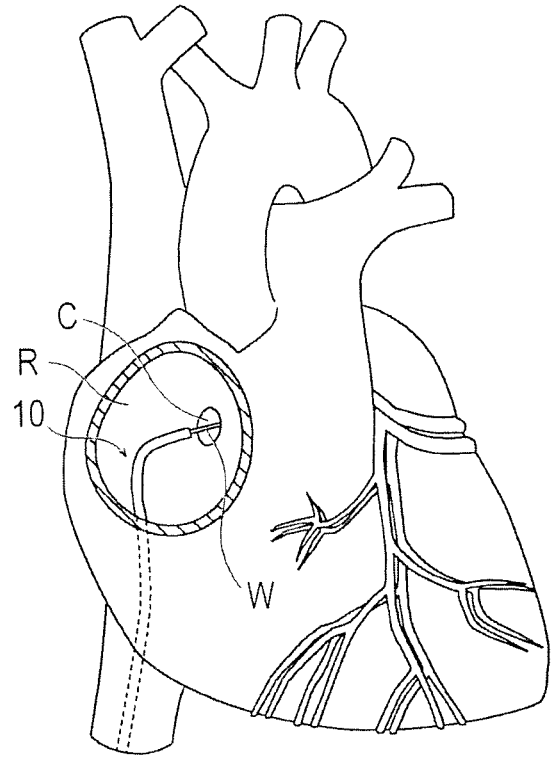
FIG. 5 is a schematic drawing illustrating a state in which the contrast agent removing device is arranged in right atrium.
Figure 6:
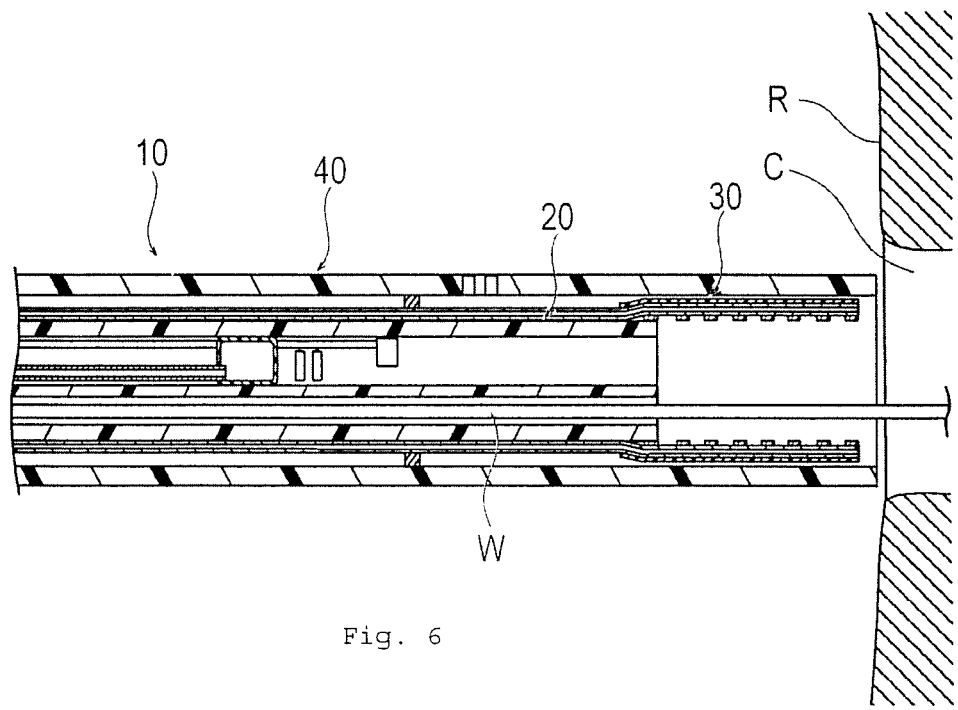
FIG. 6 is a cross-sectional view illustrating a state in which the contrast agent removing device is arranged in the vicinity of a coronary sinus in right atrium.

Next, the guide wire W is caused to reach the right atrium R, and is inserted into an exit portion of the coronary sinus C leading to the right atrium R. Subsequently, the guide wire W is inserted into the guide wire lumen 21 of the contrast agent removing device 10 thus prepared, and the contrast agent removing device 10 is inserted into vein along the guide wire W. Next, the contrast agent removing device 10 is pushed and advanced along the guide wire W, and is reached to the right atrium R as illustrated in FIGS. 5 and 6 (inserting step).

Figure 7:
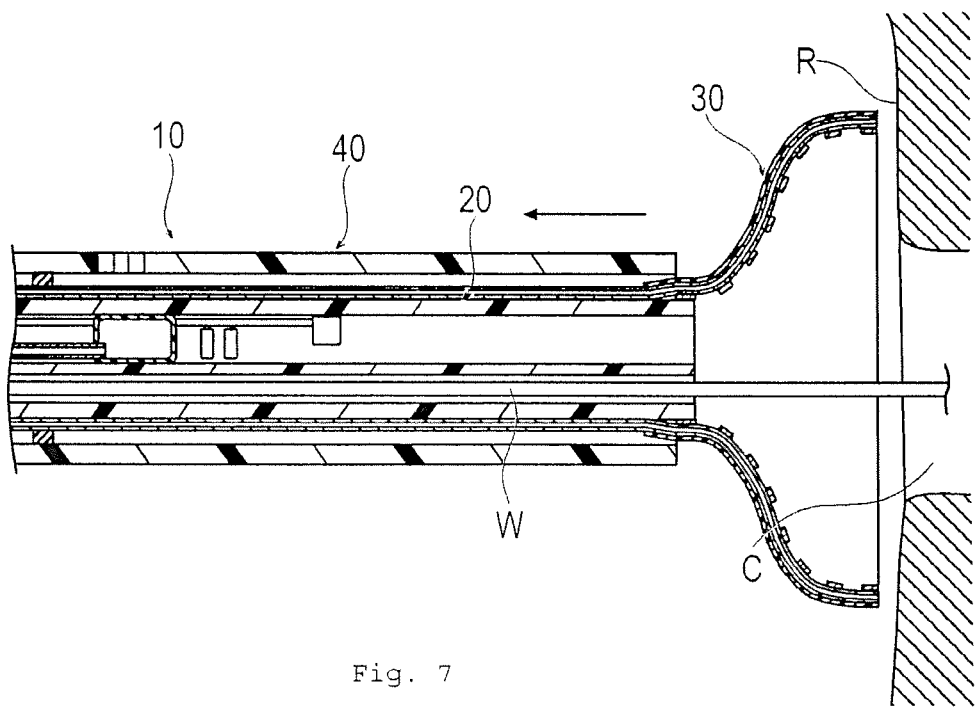
FIG. 7 is a cross-sectional view illustrating a state in which the expandable portion is expanded in right atrium.

Next, if the first operating unit 51 is moved in the proximal direction with respect to the second operating unit 52 or if the second operating unit 52 is moved in the distal direction with respect to the first operating unit 51, the expandable portion 30 expands to be larger than the exit portion of the coronary sinus C (expanding step) as illustrated in FIG. 7.

Figure 8:
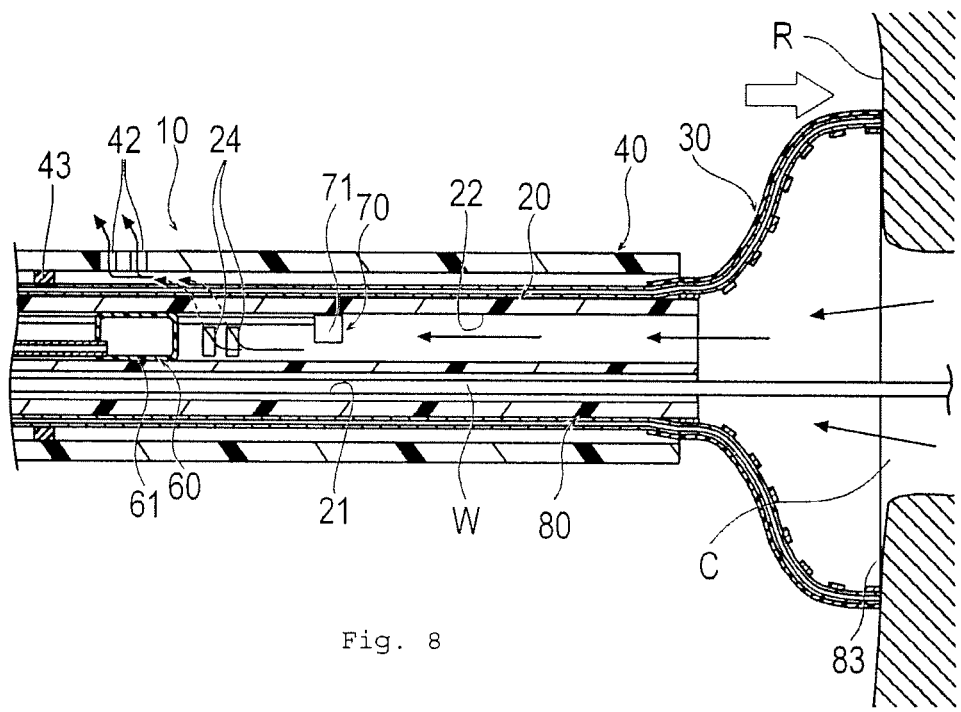
FIG. 8 is a cross-sectional view illustrating a state in which blood is returned back into a blood vessel while being guided into an interior of the contrast agent removing device.

Next, the expandable portion 30 is brought into contact with the wall surface of the right atrium R so that the expandable portion 30 covers the coronary sinus C, and the suction apparatus 93 is activated to cause the adsorption portions 83 to start sucking (Step S2). Since the guide wire W is already inserted into the coronary sinus C at this time, positioning of the adsorption portion 83 is easy. Accordingly, the adsorption portion 83 is brought into tight contact with the wall surface of the right atrium R located around the exit portion of the coronary sinus C by a negative pressure acting on the adsorption portion 83 as illustrated in FIG. 8 (fixing step). When the adsorption portion 83 is in tight contact with the right atrium R, almost all blood flowing from the coronary sinus C to the right atrium R is guided to the draining lumen 22 by the expandable portion 30 except for a small amount of blood which leaks from a gap between the right atrium R and the expandable portion 30 (introducing step). When blood is guided to the draining lumen 22, the detecting apparatus 90 detects the concentration of the contrast agent on the basis of a signal from the sensor 71. The signal from the detecting apparatus 90 is communicated to the control unit 92, and whether the concentration of the contrast agent is not higher than a predetermined threshold value is determined (Step S3).

In the case where the concentration of the contrast agent is not higher than the predetermined threshold value, the state in which the balloon 61 is dilated and the valve 60 is closed is maintained. In the state in which the valve 60 is closed, blood guided to the draining lumen 22 is guided into the outer tube 40 via the inner tube through holes 24. Since the seal member 43 is provided between the inner tube 20 and the outer tube 40, blood guided into the outer tube 40 is returned back into the right atrium R from the outer tube through holes 42 provided on the distal side with respect to the seal member 43. In this manner, blood is not drained out of the body via the draining lumen 22 as long as the concentration of the contrast agent does not exceed the threshold value, and thus occurrence of ischemia due to drainage of the blood is reduced.

Figure 9:
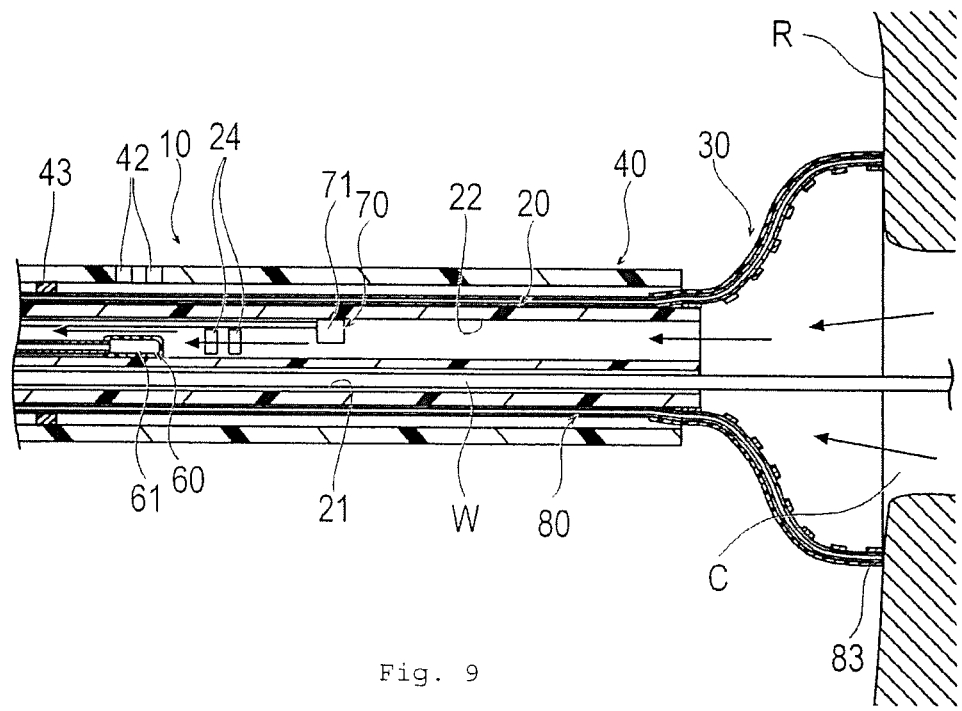
FIG. 9 is a cross-sectional view illustrating a state in which a contrast agent is drained out of a blood vessel.

Next, the contrast agent is injected from another catheter inserted into artery for the PCI into coronary artery. The contrast agent injected into the coronary artery runs through coronary vein and reaches the coronary sinus C. When the contrast agent reaches the coronary sinus C, the expandable portion 30 guides blood containing the contrast agent into the draining lumen 22 of the inner tube 20. If the concentration of the contrast agent detected by the detecting apparatus 90 on the basis of a signal from the sensor 71 exceeds the threshold value, the control unit 92 that receives the signal from the detecting apparatus 90 automatically controls the automatic injection apparatus 91, and drains a dilation fluid from the balloon 61 to open the valve 60 as illustrated in FIG. 9 (Step S4). Accordingly, blood containing the contrast agent runs through the draining lumen 22 and is drained from the drain port 55 by a blood pressure higher than the atmospheric pressure (removing step).

Whether the concentration of the contrast agent detected by the detecting apparatus 90 on the basis of a signal from the sensor 71 is not higher than the threshold value is always determined (Step S5). If the concentration of the contrast agent is lowered to a level equal to or lower than the threshold value, the control unit 92 which has received the signal from the detecting apparatus 90 automatically controls the automatic injection apparatus 91, and supplies the dilation fluid to the balloon 61 to close the valve 60 as illustrated in FIG. 8 (Step S6). Accordingly, blood guided to the draining lumen 22 is returned back to the interior of the right atrium R via the inner tube through holes 24 and the outer tube through holes 42.

The contrast agent removing device 10 operates in accordance with injection of the contrast agent into the coronary artery, and blood containing the contrast agent is drained out of the body via the draining lumen 22 only when the concentration of the contrast agent in the blood exceeds the threshold value.

Figure 10:
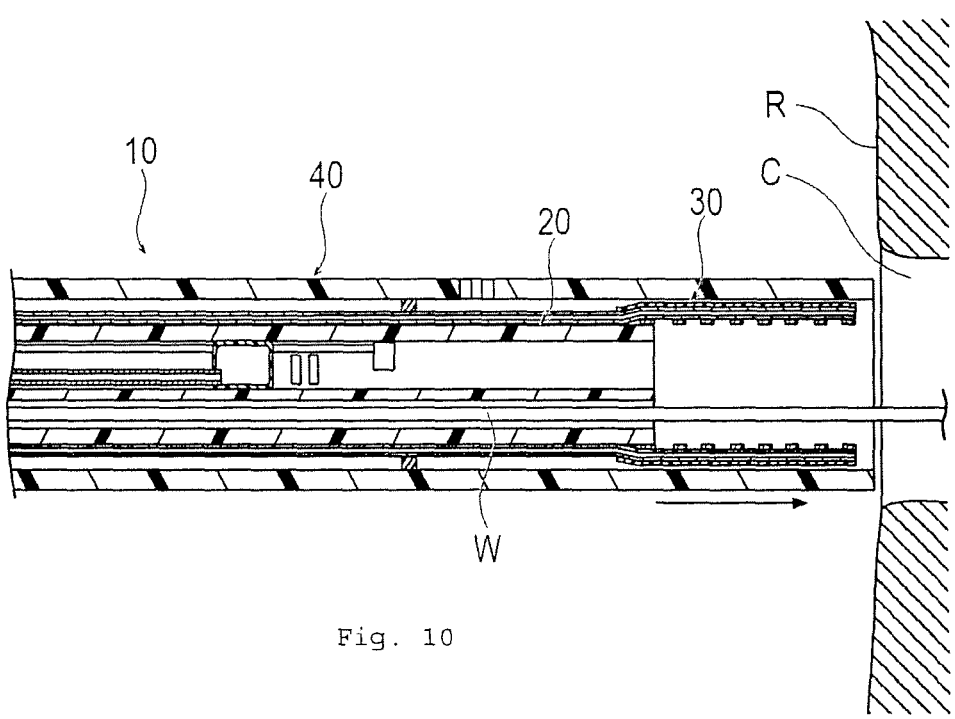
FIG. 10 is a cross-sectional view illustrating a state in which the expandable portion is moved away from an entry portion of coronary sinus in right atrium and is contracted.

After the completion of the procedure of the PCI, the suction apparatus 93 connected to the adsorption portion 83 is stopped (Step S7). Accordingly, the expandable portion 30 is moved away from the wall surface of the right atrium R. Subsequently, if the first operating unit 51 is moved in the distal direction with respect to the second operating unit 52 or if the second operating unit 52 is moved in the proximal direction with respect to the first operating unit 51, the expandable portion 30 is stored and is contracted in the outer tube 40 as illustrated in FIG. 10 (contracting step).

Subsequently, the contrast agent removing device 10 is pulled out from the introducer sheath, and the introducer sheath is removed from a vein V to complete the treatment.

As described thus far, the contrast agent removing device 10 is the contrast agent removing device 10 configured to remove the contrast agent from blood vessels, and includes the elongated outer tube 40, the inner tube 20 (inner shaft) arranged in the interior of the outer tube 40, and the expandable portion 30 interlocked with the distal portion of the inner tube 20, configured to be capable of being stored within the outer tube 40 and to expand radially outward in a funnel shape opening in the distal direction by projecting from the outer tube 40 in the distal direction; and the fixing portion 80 provided at the rim of the expandable portion 30 and configured to be capable of being fixed to a contact object.

The contrast agent removing device 10 configured as described above includes the fixing portion 80, which can be fixed to the contact object at the rim of the expandable portion 30. Accordingly, the contrast agent removing device 10 can be fixed to a wall surface of the right atrium R with the expandable portion 30 expanded so as to cover an exit of the coronary sinus C from the right atrium R side. Accordingly, the expandable portion 30 that guides blood and the contrast agent can be held at an adequate position, and thus the contrast agent flowing from the coronary sinus C to the right atrium R can be effectively trapped and removed.

To suck the contrast agent upon reaching the coronary sinus C, there is a method of stopping a blood flow by using a balloon configured to dilate in the coronary sinus C and sucking a contrast agent in the coronary sinus C with a catheter inserted into the coronary sinus C. With this method, the coronary sinus C receives a significant load from the balloon, and an outer diameter which allows insertion of the catheter into the coronary sinus C for suction is required. Consequently, it is difficult to secure a wide flow path within the catheter. In contrast, the fixing portion 80, of the the contrast agent removing device 10, can fix the expandable portion 30 while securing a wide inner diameter of the inner tube 20 which is to be arranged in the right atrium R wider than the coronary sinus C for suction. Therefore, the expandable portion 30 can be held always at an adequate position in the pulsating heart. Therefore, after blood flowing in the coronary sinus C has been introduced to the inner tube 20 as much as possible without leakage, blood other than the contrast agent can be returned back into the blood vessels. Therefore, probability of failure to remove the contrast agent which should be removed is reduced, and the contrast agent is effectively removed.

The fixing portion 80 includes the adsorption portion 83 configured to apply a negative pressure to the outside in the distal direction. In this configuration, the position of the expandable portion 30 that guides the contrast agent is held adequately by causing the adsorption portion 83 to be adhered to the wall surface of the right atrium R by the negative pressure, so that the contrast agent can be effectively removed from the interior of the blood vessels.

The inner tube 20 (inner shaft) includes the draining lumen 22 extending from the distal portion surrounded by the expandable portion 30 to the proximal portion and the inner tube side holes 24 (through holes) penetrating from the draining lumen 22 to the outer surface on the proximal side with respect to the expandable portion 30. Therefore, blood and the contrast agent are guided by the expandable portion 30 into the draining lumen 22 to drain the contrast agent out of the body, and the blood guided into the draining lumen 22 can be selectively returned to blood vessels through the through holes 24.

Since the blood guided to the draining lumen 22 can be returned back to blood vessels from the inner tube side holes 24, probability of occurrence of ischemia due to drainage of blood is reduced.

The embodiments herein also include a contrast agent removing method for removing the contrast agent from blood vessels.

The aforesaid contrast agent removing method includes (i) an inserting step for inserting a contrast agent removing device provided with an expandable portion capable of expanding radially outward at a distal portion and a fixing portion provided on a rim of the expandable portion and configured to be capable of being fixed to a contact object into a blood vessel and guiding the device to right atrium, (ii) a fixing step for expanding the expandable portion to cover an exit portion of coronary sinus from the right atrium side and fixing the fixing portion to a wall surface of the right atrium, and (iii) a removing step for removing the contrast agent from blood guided by the expandable portion.

The contrast agent removing method configured as described above is configured to expand the expandable portion to cover the exit portion of coronary sinus from the right atrium side and fix the fixing portion to the wall surface of right atrium. Therefore, the expandable portion that guides blood and the contrast agent is held at an adequate position, and thus the contrast agent flowing from the coronary sinus to the right atrium can be effectively trapped and removed.

According to the aforesaid contrast agent removing method, the fixing portion is fixed by sucking the wall surface of the right atrium by an adsorption portion which is provided on the fixing portion and configured to apply a negative pressure to the outside in the fixing step.

Accordingly, the position of the expandable portion that guides the contrast agent can be adequately held with the minimum load applied to the wall surface of the right atrium, so that the contrast agent can be effectively removed from the interior of the blood vessels.

The aforesaid contrast agent removing method further includes an introducing step for introducing blood guided by the expandable portion into the contrast agent removing device for removing the contrast agent before the removing step. In the removing step, if the introduced blood contains a contrast agent, the contrast agent is drained out from blood vessels.

Accordingly, the contrast agent can be removed effectively from the introduced blood.

In addition, the allowable amount of drainage of the contrast agent is not limited because the contrast agent is drained out of blood vessels. Therefore, even a large amount of the contrast agent can be effectively removed.

The aforesaid contrast agent removing method further includes the introducing step for introducing blood guided by the expandable portion into the contrast agent removing device for removing the contrast agent is further included before the removing step, and in the removing step, the contrast agent is adsorbed by an adsorbent which is arranged in the contrast agent removing device and is capable of adsorbing the contrast agent, and the remained blood is returned back to blood vessels.

Accordingly, the contrast agent can be effectively removed only by causing the introduced blood to pass through the adsorbent.

Note that in the example described above, in the case where the concentration of the contrast agent detected by the sensor 71 exceeds the threshold value, the control unit 92 opens the valve 60 to drain blood containing the contrast agent. However, the configuration is not limited thereto.

For example, after the injection of the contrast agent into the coronary artery, the control unit 92 may be set to open the valve 60 and drain blood at a predetermined time for a predetermined period by setting a timer.

It is also possible to confirm the contrast agent under radiography and open the valve 60 and drain blood by a manual operation.

In this configuration, the sensor 71 for detecting the contrast agent does not need to be provided.

The structure of the valve is not limited to the balloon.

A suction apparatus such as a pump for sucking the contrast agent may be interlocked with the drain port 55 for draining the contrast agent.

A contrast agent removing device 100 may also be modified in that the contrast agent is not drained out of the body.

Note that portions or element of the contrast agent removing device 100 having the same functions as those described above are denoted by the same reference numerals and description is omitted.

Figure 12:
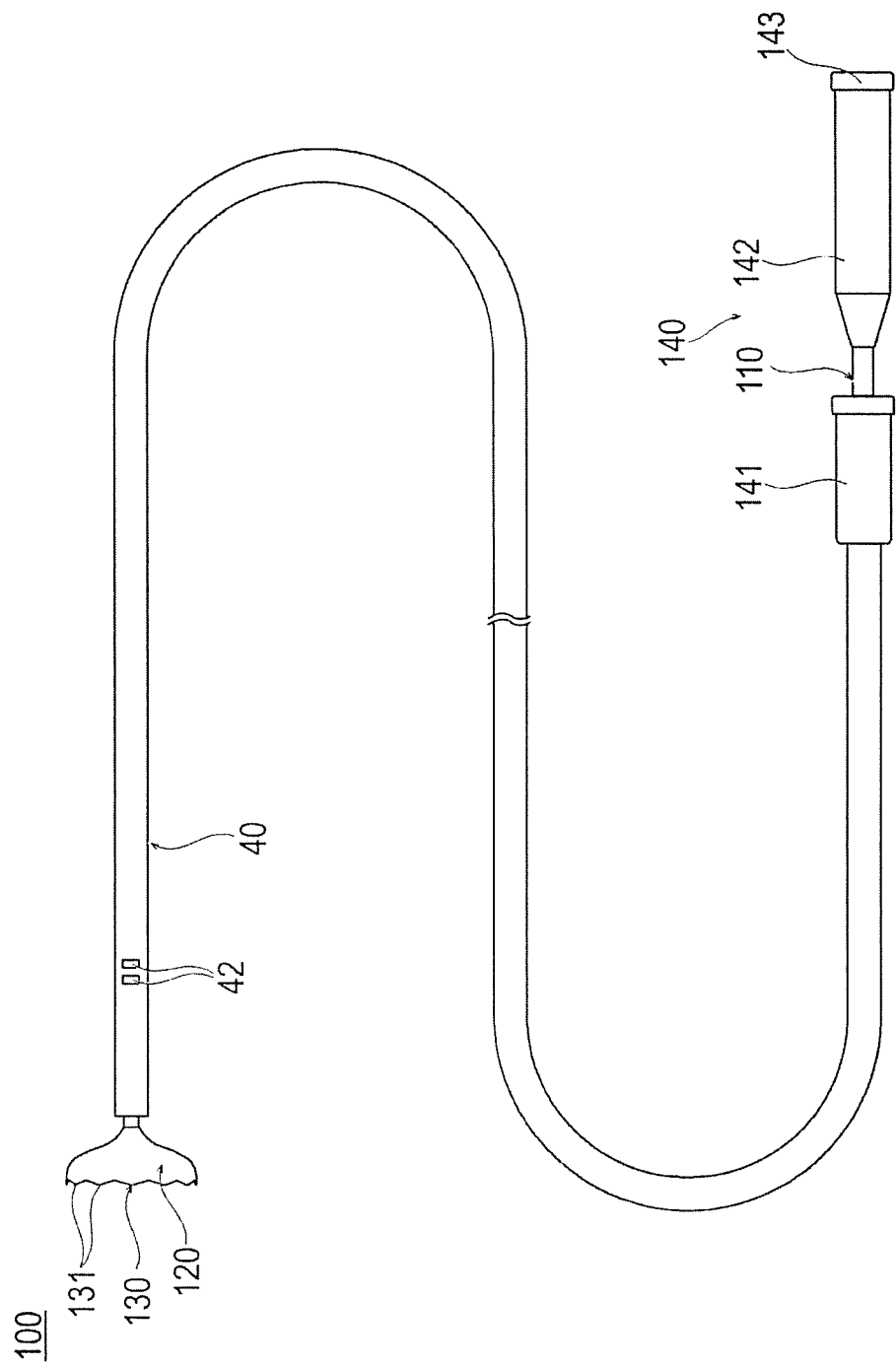
FIG. 12 is a plan view illustrating a contrast agent removing device.
Figure 13:
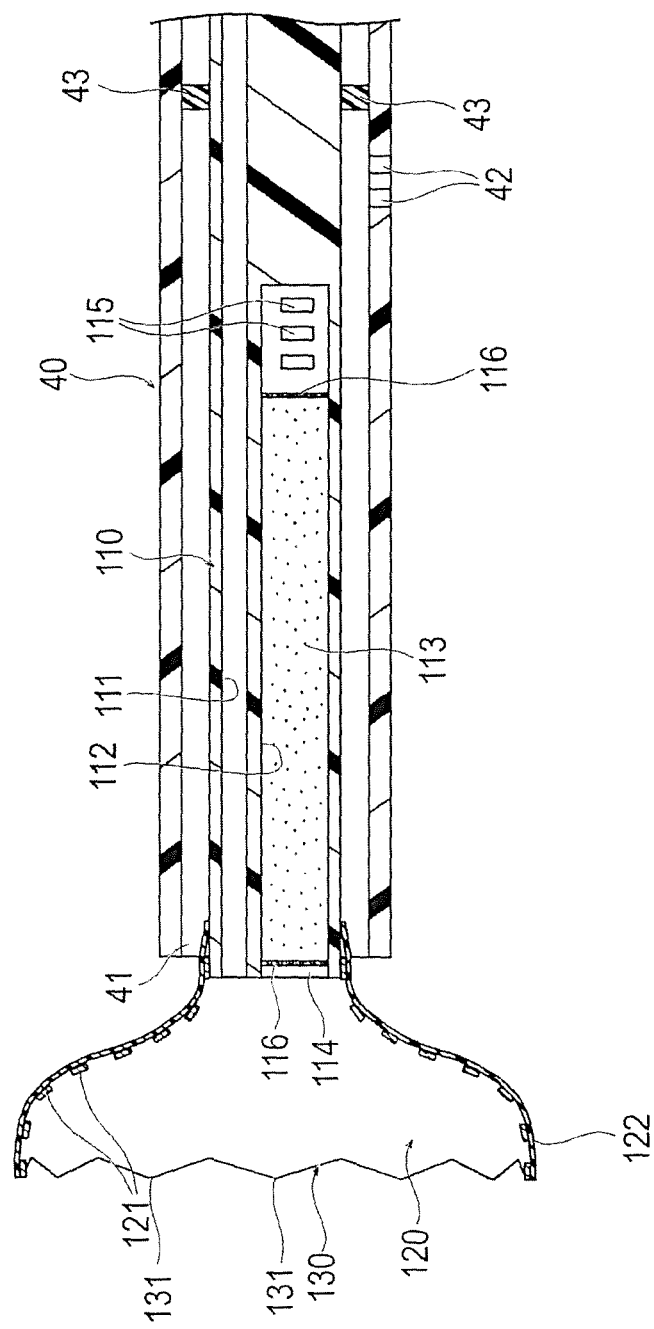
FIG. 13 is a vertical cross-sectional view illustrating a state in which an expandable portion of the contrast agent removing device is expanded.
Figure 14:
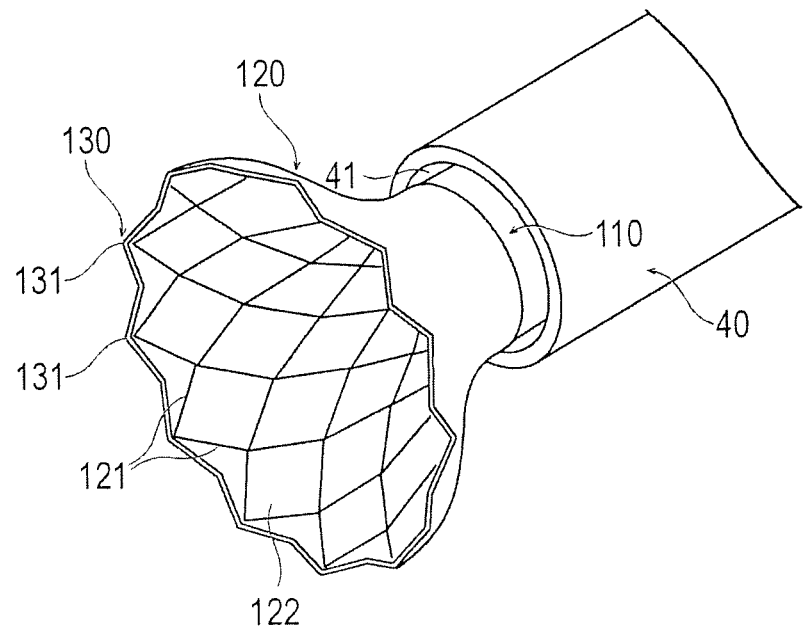
FIG. 14 is a perspective view illustrating a distal portion of the contrast agent removing device.

The contrast agent removing device 100 includes an inner tube 110 (inner shaft), the outer tube 40 configured to allow storage of the inner tube 110 in the interior thereof, an expandable portion 120 configured to be expandable and contractable at a distal portion of the inner tube 110, a fixing portion 130 configured to fix the expandable portion 120 to a biological tissue, and an operating unit 140 for operating the expandable portion 120 as illustrated in FIGS. 12 to 14.

The inner tube 110 is an elongated tubular member and includes a guide wire lumen 111 which allows insertion of a guide wire in the interior thereof, and a storage portion 112 for storing a adsorbent 113 that adsorbs the contrast agent.

The storage portion 112 opens at an inner tube distal side opening 114 at the distal portion of the inner tube 110, and opens to the side by inner tube through holes 115 (through holes) penetrating from an inner surface of the inner tube 110 to an outer surface thereof at a predetermined position on the proximal side with respect to the inner tube distal side opening 114.

The expandable portion 120 is interlocked with the distal portion of the inner tube 110.

A second operating unit 142 which constitutes part of the operating unit 140 is fixed to the proximal portion of the inner tube 110.

The expandable portion 120 includes wire members 121 formed of elastically deformable wires and forming a net shape and a film portion 122 which covers the wire members 121 so as to close void portions between the wire members 121.

The expandable portion 120 is formed in a funnel shape so as to project in the distal direction from the distal portion of the inner tube 110.

Figure 15:
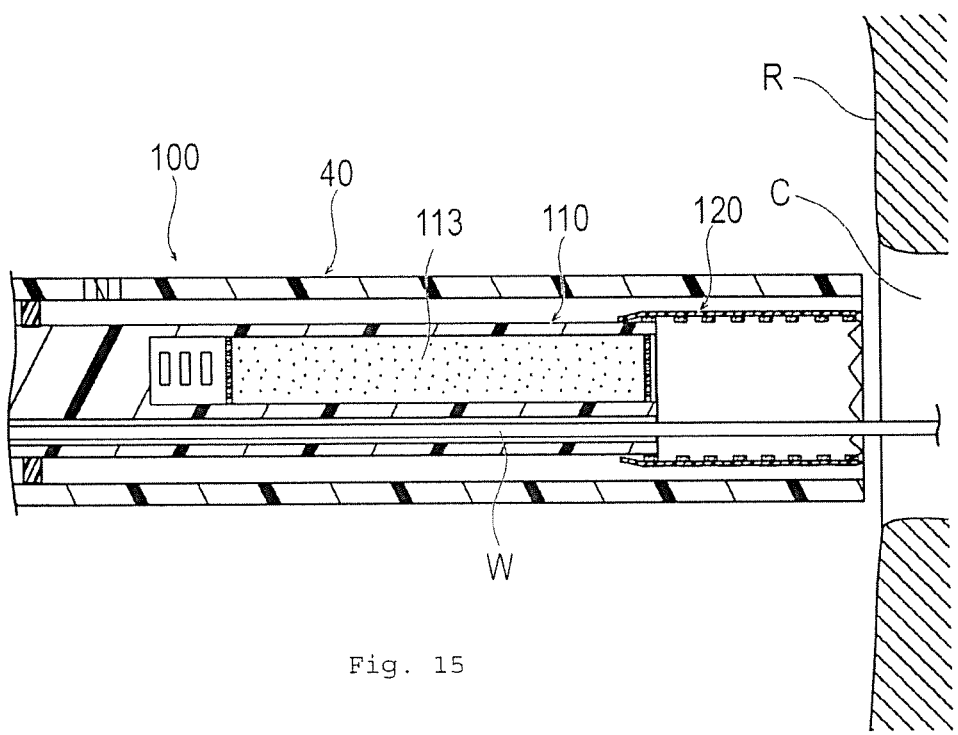
FIG. 15 is a cross-sectional view illustrating a state in which the contrast agent removing device is arranged in the vicinity of coronary sinus in right atrium.

The expandable portion 120 is stored in the outer tube 40 while being elastically deformed and contracted as illustrated in FIG. 15 by operating the operating unit 140 to move the inner tube 110 in a proximal direction relatively with respect to the outer tube 40.

The expandable portion 120 is elastically expandable so as to project from the outer tube 40 in the distal direction and expands radially outward from the inner tube distal side opening 114 of the inner tube 110 as illustrated in FIGS. 12 to 14 by operating the operating unit 140 and moving the inner tube 110 in the distal direction relatively with respect to the outer tube 40.

The fixing portion 130 is a portion for fixing the expandable portion 120 to a biological tissue, and is formed at a distal edge of the expandable portion 120.

The fixing portion 130 is provided with a plurality of projecting portions 131 projecting in the distal direction.

The projecting portions 131 are formed, for example, by the wire members 121 intersecting with each other and projecting in the distal direction as illustrated in FIG. 14.

The projecting portions 131 dig into and catch the biological tissue, so that the state in which the expandable portion 120 is in tight contact with the biological tissue is effectively maintained.

The adsorbent 113 is held by being tightly interposed between filters 116 which allow passage of blood and the contrast agent in the interior of the storage portion 112 as illustrated in FIG. 13.

The adsorbent 113 is a water-insoluble contrast agent adsorbent which physicochemically adsorbs the contrast agent.

The adsorbent 113 is preferably a porous member from a point that a specific surface sufficient for adsorbing the contrast agent is ensured.

The porous member is a member having a number of continuous or discontinuous holes.

Since the amount of adsorption of the contrast agent is large, the adsorbent having a surface not smaller than 800 $m^2/g$ can beused.

Examples of the porous member include silica gel, alumina gel, zeolite, and active charcoal. The porous member can also be active charcoal because of its large specific surface.

As the shape of the adsorbent 113, any of a spherical type, a grain type, a fiber type, a hollow fiber type, and a flat film type may be effectively used. However, the spherical type or the grain type can be used in terms of a blood circulation surface during extracorporeal circulation.

The adsorbent 113 comes into contact with blood, and blood coagulates upon contact with foreign substances.

Therefore, the adsorbent 113 may be subjected to a surface treatment for controlling adhesion of blood platelet for improving an affinity with blood.

For example, the adsorbent 113 provided with a coating layer formed of a material having low adhesiveness for blood platelet on the surface thereof which comes into contact with blood can beused.

The operating unit 140 is provided with a first operating unit 141 interlocked with a proximal end portion of the outer tube 40 and the second operating unit 142 interlocked with a proximal end portion of the inner tube 110 as illustrated in FIG. 12.

The inner tube 110 penetrates through the first operating unit 141 so as to be movable in the axial direction.

The second operating unit 142 is provided with a guide wire port 143 which communicates with the guide wire lumen 111 of the inner tube 110. The guide wire port 143 allows insertion of a guide wire.

Next, a method of using the contrast agent removing device 100 according to the modified contrast agent removing device 100 will be described.

Firstly, the contrast agent removing device 100 to be used is primed, and the interior is substituted by physiological salt solution.

In this initial state, the expandable portion 120 is folded and stored in the outer tube 40 (see FIG. 15).

Next, an introducer sheath (not illustrated) is inserted into femoral vein or cervical vein.

Next, the guide wire W is inserted into vein via the introducer sheath.

Note that the position where the introducer sheath is to be installed is not limited as long as the contrast agent removing device 100 is allowed to access the right atrium R.

Next, the guide wire W is caused to reach the right atrium R, and is inserted into an exit portion of the coronary sinus C leading to the right atrium R.

Subsequently, the guide wire W is inserted into the guide wire lumen 111 of the contrast agent removing device 100 thus prepared, and the contrast agent removing device 100 is inserted into vein along the guide wire W.

Next, the contrast agent removing device 100 is pushed and advanced along the guide wire W, and is reached to the right atrium R as illustrated in FIG. 15 (inserting step).

Figure 16:
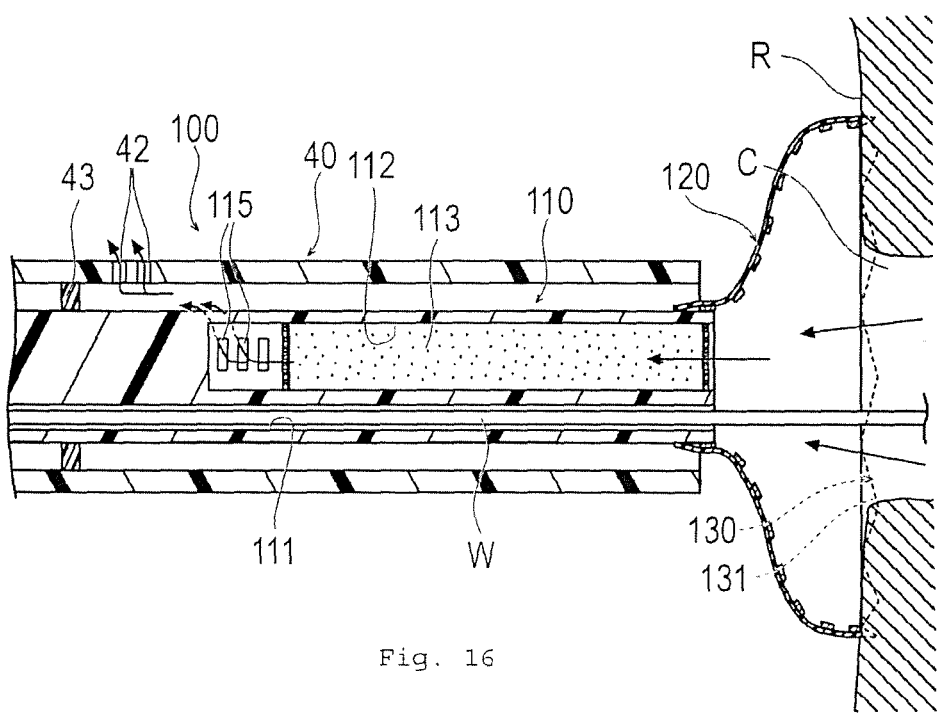
FIG. 16 is a cross-sectional view illustrating a state in which blood is returned back into a blood vessel while being guided into an interior of the contrast agent removing device.

Next, if the first operating unit 141 is moved in the proximal direction with respect to the second operating unit 142 or if the second operating unit 142 is moved in the distal direction with respect to the first operating unit 141, the expandable portion 120 expands to be larger than the exit portion of the coronary sinus C as illustrated in FIG. 16 (expanding step).

Next, when the expandable portion 120 is brought into contact with the wall surface of the right atrium R so that the expandable portion 120 covers the coronary sinus C, the projecting portions 131 of the fixing portion 130 provided on the rim of the expandable portion 120 dig into and catch the biological tissue, and the state in which the expandable portion 120 is in tight contact with the biological tissue is effectively maintained (fixing step).

When the expandable portion 120 comes into tight contact with the right atrium R, all blood flowing from the coronary sinus C to the right atrium R except for a small amount of blood which leaks from a gap between the right atrium R and the expandable portion 120 is guided into the storage portion 112 by the expandable portion 120 (introducing step).

When blood is introduced into the storage portion 112, the blood passes through void portions in the adsorbent 113 and is guided into the outer tube 40 via the inner tube through holes 115.

Since the seal member 43 is provided between the inner tube 110 and the outer tube 40, blood guided into the outer tube 40 is returned back into the right atrium R or into vein of an access route (vain in which the contrast agent removing device 100 is inserted) from the outer tube through holes 42 provided on the distal side with respect to the seal member 43.

Next, a contrast agent is injected into the coronary artery for the PCI.

The contrast agent injected into the coronary artery runs through coronary vein and reaches the coronary sinus C.

When the contrast agent reaches the coronary sinus C, blood containing the contrast agent is guided into the storage portion 112 of the inner tube 110 by the expandable portion 120.

If the blood contains the contrast agent, the contrast agent is adsorbed by the adsorbent 113 in the storage portion 112 (removing step), and only blood from which the contrast agent is removed passes through the inner tube through holes 115 and the outer tube through holes 42 and is returned back into the right atrium R or the vein in the access route.

After the completion of the procedure of the PCI, the fixing portion 130 is separated from a portion surrounding the exit of the coronary sinus C of the right atrium R.

Subsequently, if the first operating unit 141 is moved in the distal direction with respect to the second operating unit 142 or if the second operating unit 142 is moved in the proximal direction with respect to the first operating unit 141, the expandable portion 120 is contracted and stored in the outer tube 40 as illustrated in FIG. 15.

Subsequently, the contrast agent removing device 100 is pulled out from the introducer sheath, and the introducer sheath is removed from the vein V to complete the treatment.

As described thus far, the contrast agent removing device 100 according to the second embodiment includes the adsorbent 113 in the interior of the inner tube 110, the adsorbent 113 selectively adsorbs and removes the contrast agent from blood containing the contrast agent, so that the blood after the removal of the contrast agent can be returned back into the right atrium R or to vein of the access route via the inner tube through holes 115 and the outer tube through holes 42.

The fixing portion 130 includes the projecting portions 131 projecting in the distal direction. Therefore, the position of the expandable portion 120 that guides the contrast agent is held adequately by causing the projecting portions 131 to dig into the wall surface of the right atrium R, so that the contrast agent can be effectively removed from the interior of the blood vessels.

The inner tube 110 (inner shaft) includes the storage portion 112, which corresponds to a space extending from the distal portion surrounded by the expandable portion 120 in the proximal direction, the inner tube through holes 115 (through holes) on the proximal side with respect to the expandable portion 120 and penetrate from the storage portion 112 to the outer surface, and the adsorbent 113 arranged in the storage portion 112 and configured to be capable of adsorbing the contrast agent.

Accordingly, blood and the contrast agent are guided to the storage portion 112 by the expandable portion 120, the contrast agent is adsorbed by the adsorbent 113, and blood passed through the adsorbent 113 is returned from the inner tube through holes 115 into the blood vessels.

According to the contrast agent removing method above, the fixing step includes fixing the fixing portion by causing the projecting portions provided on the fixing portion and projecting in the distal direction to dig into the wall surface of the right atrium.

Accordingly, the position of the expandable portion that guides the contrast agent can be adequately held, and the contrast agent can be effectively removed from the interior of the blood vessels.

Another modified contrast agent removing device 150 may be different from that of those configurations above in that the contrast agent is not drained out of the body.

Note that portions having the same functions as those above are denoted by the same reference numerals and description is omitted.

Figure 17:
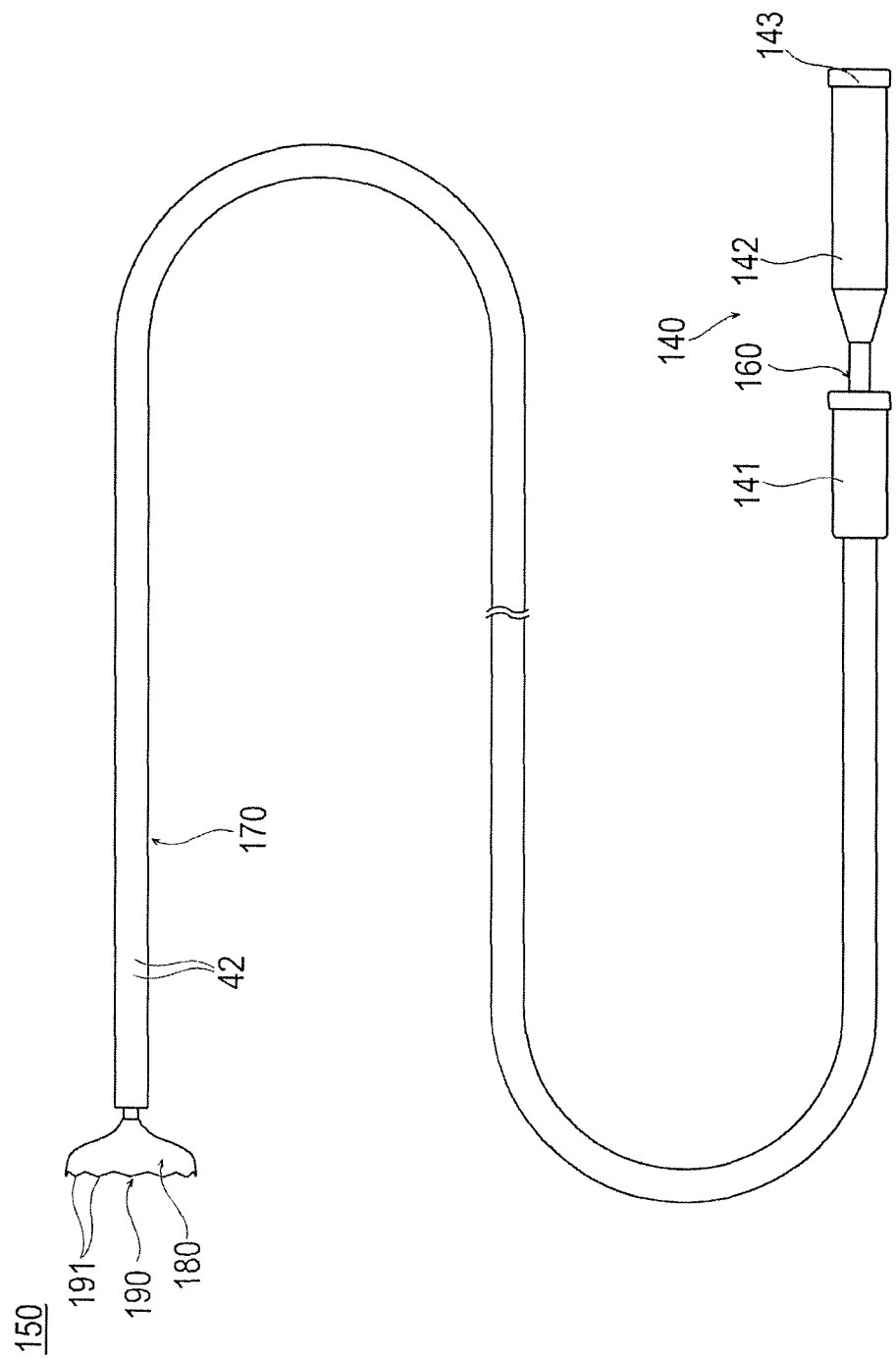
FIG. 17 is a plan view illustrating a contrast agent removing device according to a third embodiment.
Figure 18:
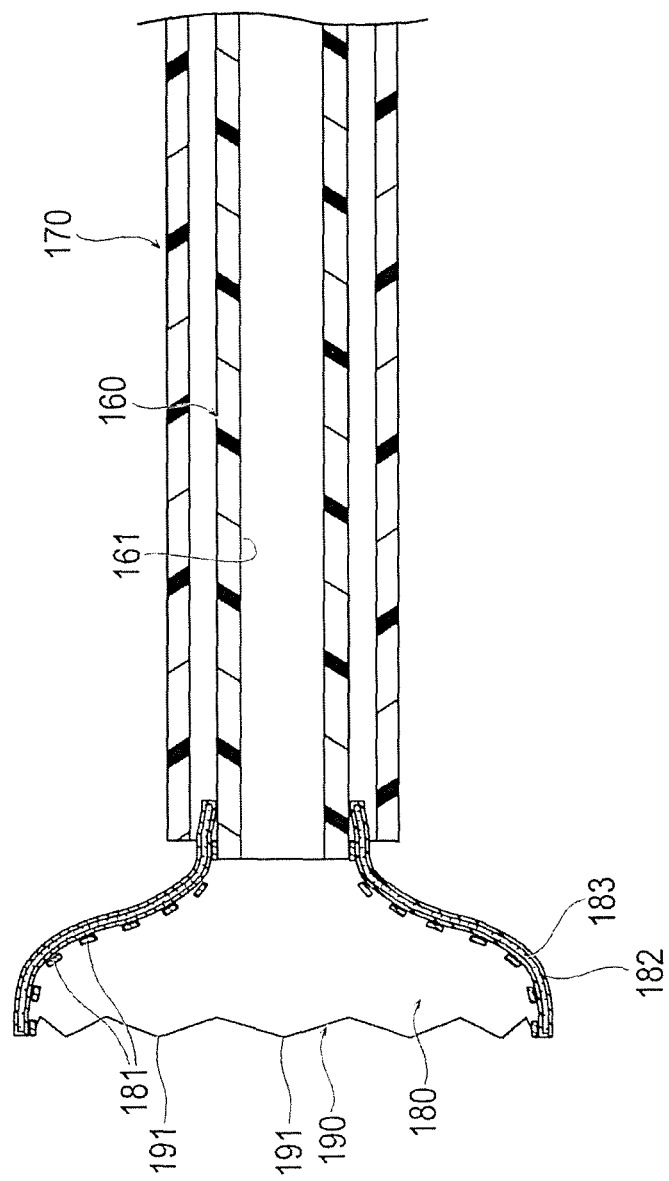
FIG. 18 is a vertical cross-sectional view illustrating a state in which an expandable portion of the contrast agent removing device is expanded.

The contrast agent removing device 150 includes an inner tube 160, an outer tube 170 configured to allow storage of the inner tube 160 in the interior thereof, an expandable portion 180 configured to be expandable and contractable at a distal portion of the inner tube 160, a fixing portion 190 configured to fix the expandable portion 180 to a biological tissue, and the operating unit 140 for operating the expandable portion 180 as illustrated in FIGS. 17 and 18.

The inner tube 160 is an elongated tubular member and includes a guide wire lumen 161 which allows insertion of a guide wire in the interior thereof.

The expandable portion 180 is interlocked with the distal portion of the inner tube 160.

The second operating unit 142 which constitutes part of the operating unit 140 is fixed to the proximal portion of the inner tube 160.

The outer tube 170 is an elongated tubular member configured to allow storage of the inner tube 160 and the expandable portion 180 in the interior thereof, and to be movable in an axial direction relatively with respect to the inner tube 160.

The proximal portion of the outer tube 170 is interlocked with the first operating unit 141 which constitutes part of the operating unit 140.

The expandable portion 180 includes wire members 181 formed of elastically deformable wires and forming a net shape, a filter 182 configured to cover the wire members 181 so as to close void portions between the wire members 181, and a adsorbent 183 arranged in the interior of the filter 182.

The expandable portion 180 is formed in a funnel shape so as to project in the distal direction from the distal portion of the inner tube 160.

The filter 182 is a member which allows circulation of blood therethrough, and the adsorbent 183 is arranged in the interior of the filter 182 in a sandwiched manner.

Note that the adsorbent 183 may be held so as to be adhered to the outer surface or the inner surface of the filter.

Figure 19:
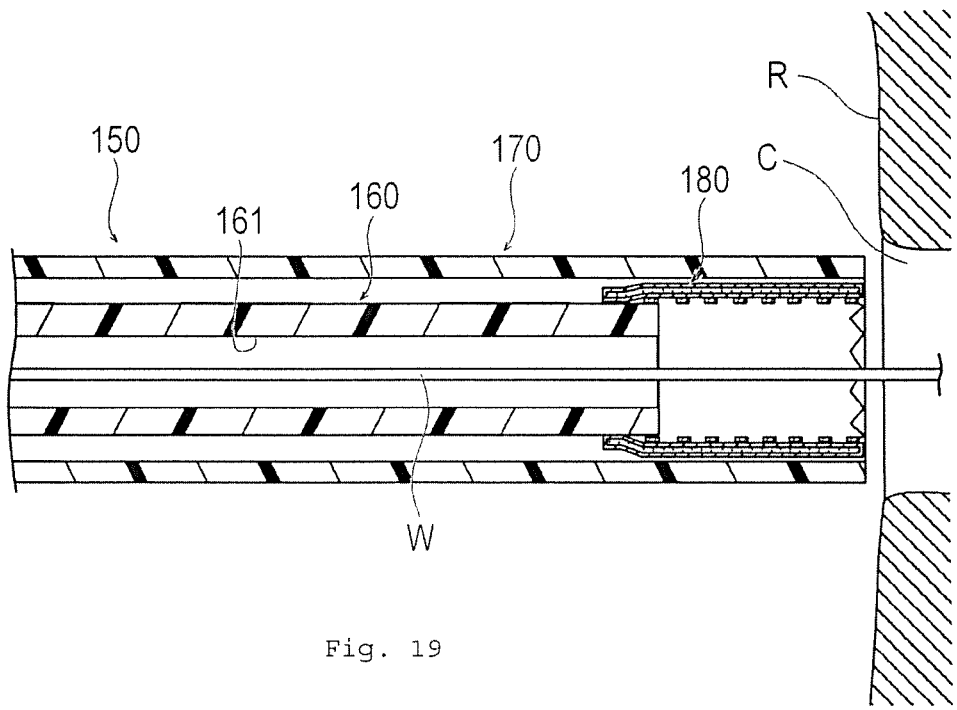
FIG. 19 is a cross-sectional view illustrating a state in which the contrast agent removing device is arranged in the vicinity of a coronary sinus in right atrium.

The expandable portion 180 is stored in the outer tube 170 while being elastically deformed and contracted as illustrated in FIG. 19 by operating the operating unit 140 to move the inner tube 160 in a proximal direction relatively with respect to the outer tube 170.

The expandable portion 180 is elastically expandable so as to project from the outer tube 170 in the distal direction and expand radially outward from the inner tube distal side opening 114 of the inner tube 160, as illustrated in FIGS. 17 and 18, by operating the operating unit 140 and moving the inner tube 160 in the distal direction relatively with respect to the outer tube 170.

The fixing portion 190 is a portion for fixing the expandable portion 180 to a biological tissue, and is formed at a distal end portion of the expandable portion 180.

The fixing portion 190 is provided with a plurality of projecting portions 191 projecting in the distal direction.

The projecting portions 191 are formed by the wire members 181 intersecting with each other and projecting in the distal direction in the same manner as described above.

The projecting portions 191 dig into and catch the biological tissue, so that the state in which the expandable portion 180 is in tight contact with the biological tissue is effectively maintained.

The operating unit 140 is provided with the first operating unit 141 interlocked with a proximal end portion of the outer tube 170 and the second operating unit 142 interlocked with a proximal end portion of the inner tube 160. The inner tube 160 penetrates through the first operating unit 141 so as to be movable in the axial direction.

The second operating unit 142 is provided with the guide wire port 143 which communicates with the guide wire lumen 161 of the inner tube 160. The guide wire port 143 allows insertion of a guide wire.

Next, a method of using the above modified contrast agent removing device 150 will be described.

Firstly, the contrast agent removing device 150 to be used is primed, and the interior is substituted by physiological salt solution. In this initial state, the expandable portion 180 is contracted and stored in the outer tube 170 as illustrated in FIG. 19.

Next, an introducer sheath (not illustrated) is inserted into femoral vein or cervical vein. Next, the guide wire W is inserted into vein via the introducer sheath. Note that the position where the introducer sheath is to be installed is not limited as long as the contrast agent removing device 150 is allowed to access from the right atrium R to the coronary sinus C.

Next, the guide wire W is caused to reach the right atrium R, and is inserted into an exit portion of the coronary sinus C.

Next, the guide wire W is inserted into the guide wire lumen 161 of the contrast agent removing device 150 thus prepared, and the contrast agent removing device 150 is inserted into vein along the guide wire W. Subsequently, the contrast agent removing device 150 is pushed and advanced along the guide wire W, and is reached to the right atrium R as illustrated in FIG. 19 (inserting step).

Figure 20:
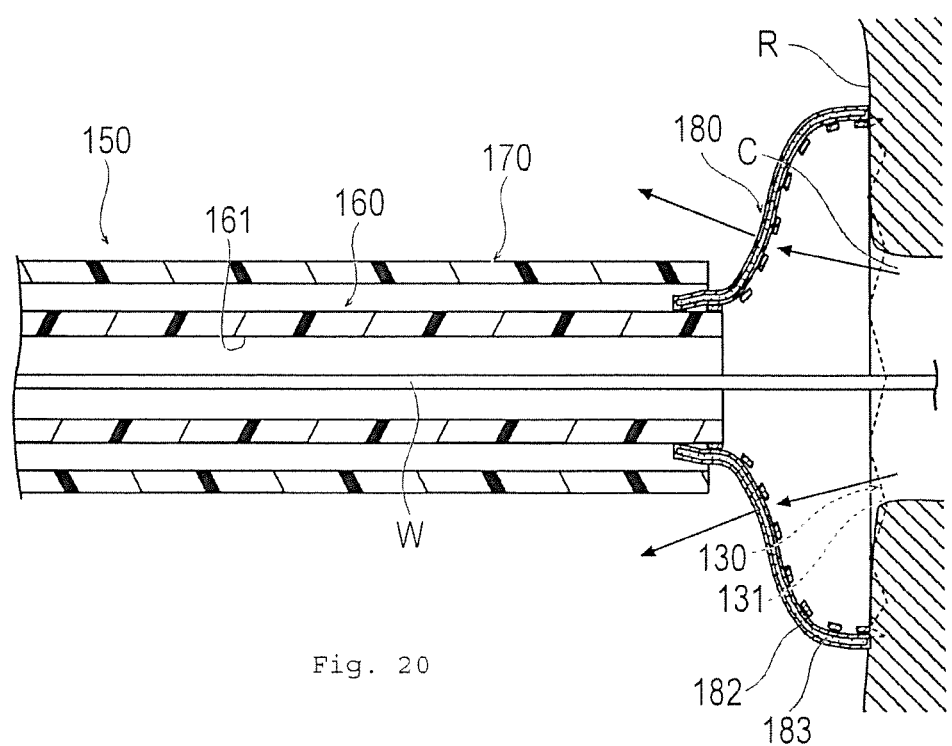
FIG. 20 is a cross-sectional view illustrating a state in which blood is returned back into a blood vessel while being guided into an interior of the contrast agent removing device.

Next, if the first operating unit 141 is moved in the proximal direction with respect to the second operating unit 142 or if the second operating unit 142 is moved in the distal direction with respect to the first operating unit 141, the expandable portion 180 expands to be larger than the exit portion of the coronary sinus C as illustrated in FIG. 20 (expanding step).

Next, when the expandable portion 180 is brought into contact with the wall surface of the right atrium R so that the expandable portion 180 covers the coronary sinus C, the projecting portions 191 provided on the distal portion of the expandable portion 180 dig into and catch the biological tissue, and the state in which the expandable portion 180 is in tight contact with the biological tissue is effectively maintained (fixing step). When the expandable portion 180 comes into tight contact with the right atrium R, all blood flowing from the coronary sinus C to the right atrium R except for a small amount of blood which leaks from a gap between the right atrium R and the expandable portion 180 passes through the filter 182 of the expandable portion 180. The blood passing through the filter 182 passes through void portions in the adsorbent 183 and reaches the right atrium R (introducing step). Note that the guide wire lumen 161 is occluded at the proximal portion by a valve body or the like which allows insertion of the guide wire W, and thus the blood guided by the expandable portion does not flow into the guide wire W.

Next, a contrast agent is injected into the coronary artery for the PCI. The contrast agent injected into the coronary artery runs through coronary vein and reaches the coronary sinus C. When the contrast agent reaches the coronary sinus C, blood containing the contrast agent passes through the filter 182 of the expandable portion 180. If the blood contains the contrast agent, the contrast agent is adsorbed by the adsorbent 183 in the filter 182 (removing step) and only blood from which the contrast agent is removed reaches the interior of the right atrium R.

After the completion of the procedure of the PCI the fixing portion 190 is separated from a portion surrounding the exit of the coronary sinus C of the right atrium R. Subsequently, if the first operating unit 141 is moved in the distal direction with respect to the second operating unit 142 or if the second operating unit 142 is moved in the proximal direction with respect to the first operating unit 141, the expandable portion 180 is contracted and stored in the outer tube 170 as illustrated in FIG. 19 (contracting step).

Subsequently, the contrast agent removing device 150 is pulled out from the introducer sheath, and the introducer sheath is removed from the vein V to complete the treatment.

As described above, according to the contrast agent removing device 150 described above, the expandable portion 180 allows liquid to flow from a distal surface side toward a proximal surface side in an expanded state and the adsorbent 183 capable of adsorbing the contrast agent is arranged. Accordingly, the contrast agent out of a mixture of blood and the contrast agent flowing in the expandable portion 180 is adsorbed by the adsorbent 183, and the blood that has passed through the adsorbent 183 is returned back to blood vessels.

Figure 21:
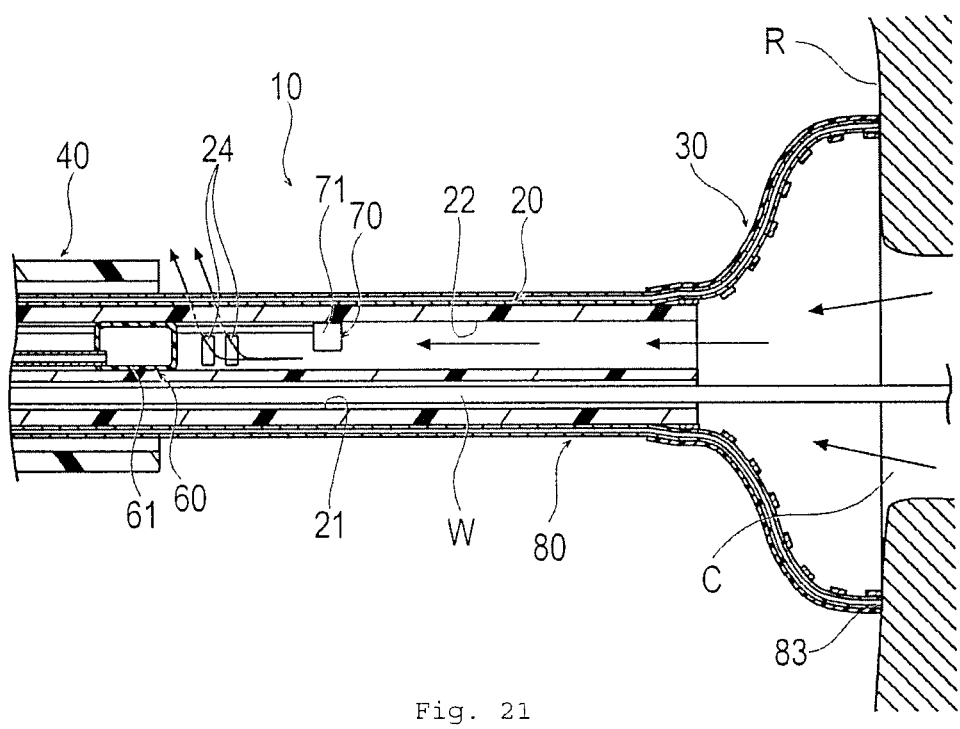
FIG. 21 is a perspective view illustrating a modification of the expandable portion of the contrast agent removing device.

Note that the present invention is not limited only to the embodiments described above, and various modifications may be made by skills in the art within a technical scope of the present invention. For example, in at least some of the embodiments above, the blood flowed through the inner tube through holes 24 into the outer tube 40 is returned back to blood vessels via the outer tube through holes 42. However, by moving a distal end portion of the outer tube 40 to the proximal side with respect to the inner tube through holes 24 as illustrated in FIG. 21, blood which has passed through the inner tube through holes 24 can be returned back into blood vessels without the intermediary of the outer tube through holes 42. In this case, the seal member 43 (see FIGS. 2 and 13) does not have to be provided.

The expandable portion does not necessarily have to be positioned entirely in the right atrium R, and a configuration in which part of the expandable portion enters from the right atrium R into the coronary sinus C is also applicable.

DESCRIPTION OF REFERENCE SIGNS 10, 100, 150 contrast agent removing device
20, 110, 160 inner tube (inner tube shaft)
22 draining lumen
23 inner tube distal side opening
24, 115 inner tube through holes (through holes)
30, 120, 180 expandable portion
40, 170 outer tube
60 valve
70 detecting portion
80, 130, 190 fixing portion
81 suction lumen
82 adsorbing opening
83 adsorption portion
112 storage portion
113, 183 adsorbent
114 inner tube distal side opening
131, 191 projecting portion
C coronary sinus
R right atrium
W guide wire

What is claimed is:

1. A contrast agent removing device for removing a contrast agent from a blood vessel, comprising:
an elongated outer tube;
an inner shaft arranged in an interior of the outer tube;
an expandable portion interlocked with a distal portion of the inner shaft and configured to be capable of being stored in the interior of the outer tube and to expand radially outward into a funnel shape opening in a distal direction by projecting in the distal direction from the outer tube, wherein the inner shaft includes a storage portion, which corresponds to a space extending from the distal portion surrounded by the expandable portion in a proximal direction;
an adsorbent arranged within the storage portion and configured to be capable of adsorbing the contrast agent; and
a fixing portion provided at a rim of the expandable portion and configured to be capable of being fixed to a contact object.

2. The contrast agent removing device according to claim 1, wherein the fixing portion includes an adsorption portion opening in the distal direction and configured to apply a negative pressure to a portion of the contact object within the rim of the expandable portion.

3. The contrast agent removing device according to claim 2, wherein the fixing portion includes a projecting portion projecting in the distal direction.

4. The contrast agent removing device according to claim 3, wherein the inner shaft includes a draining lumen extending from the distal portion surrounded by the expandable portion to a proximal portion, and a through hole formed on a proximal side with respect to the expandable portion and penetrating from the draining lumen to an outer surface.

5. The contrast agent removing device according to claim 2, wherein the inner shaft includes a draining lumen extending from the distal portion surrounded by the expandable portion to a proximal portion, and a through hole formed on a proximal side with respect to the expandable portion and penetrating from the draining lumen to an outer surface.

6. The contrast agent removing device according to claim 2, wherein the inner shaft includes a through hole formed on the proximal side with respect to the expandable portion and penetrating from the expandable portion to an outer surface.

7. The contrast agent removing device according to claim 1, wherein the fixing portion includes a projecting portion projecting in the distal direction.

8. The contrast agent removing device according to claim 1, wherein the inner shaft includes a draining lumen extending from the distal portion surrounded by the expandable portion to a proximal portion, and a through hole formed on a proximal side with respect to the expandable portion and penetrating from the draining lumen to an outer surface.

9. The contrast agent removing device according to claim 1, wherein the inner shaft includes a through hole formed on the proximal side with respect to the expandable portion and penetrating from the expandable portion to an outer surface.

10. A contrast agent removing device for removing a contrast agent from a blood vessel, comprising:
an elongated outer tube;
an inner shaft arranged in an interior of the outer tube;
an expandable portion interlocked with a distal portion of the inner shaft and configured to be capable of being stored in the interior of the outer tube and to expand radially outward into a funnel shape opening in a distal direction by projecting in the distal direction from the outer tube, wherein the expandable portion includes an adsorbent which allows circulation of liquid from a distal surface side to a proximal surface side in an expanded state of the expandable portion, and wherein the adsorbent is capable of adsorbing the contrast agent; and
a fixing portion provided at a rim of the expandable portion and configured to be capable of being fixed to a contact object.

11. The contrast agent removing device according to claim 10, wherein the expandable portion includes a filter which allows circulation of liquid therethrough.

12. The contrast agent removing device according to claim 11, wherein the adsorbent is arranged in an interior of the filter.

13. The contrast agent removing device according to claim 12, wherein the fixing portion includes a projecting portion projecting in the distal direction.

* * * * *